United States Patent
Kawabata

(10) Patent No.: US 10,130,675 B2
(45) Date of Patent: Nov. 20, 2018

(54) WOUND HEALING AGENT

(71) Applicant: SANYO CHEMICAL INDUSTRIES, LTD., Kyoto (JP)

(72) Inventor: Shingo Kawabata, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 265 days.

(21) Appl. No.: 14/767,391

(22) PCT Filed: Feb. 20, 2014

(86) PCT No.: PCT/JP2014/054026
§ 371 (c)(1),
(2) Date: Aug. 12, 2015

(87) PCT Pub. No.: WO2014/129541
PCT Pub. Date: Aug. 28, 2014

(65) Prior Publication Data
US 2016/0106801 A1   Apr. 21, 2016

(30) Foreign Application Priority Data
Feb. 22, 2013 (JP) ................. 2013-032701

(51) Int. Cl.
*A61K 38/10* (2006.01)
*A61K 38/08* (2006.01)
*C07K 14/00* (2006.01)

(52) U.S. Cl.
CPC .............. *A61K 38/08* (2013.01); *A61K 38/10* (2013.01); *C07K 14/00* (2013.01)

(58) Field of Classification Search
CPC ................................ A61K 38/08; A61K 38/10
See application file for complete search history.

(56) References Cited

U.S. PATENT DOCUMENTS 6,033,654 A * 3/2000 Stedronsky ........... A61L 24/106 106/124.1
2005/0202069 A1   9/2005 Kurokawa et al.

FOREIGN PATENT DOCUMENTS

| EP | 2 676 683 | 12/2013 | |
| JP | 6-9373 | 1/1994 | |
| JP | 9-509840 | 10/1997 | |
| JP | 10-80438 | 3/1998 | |
| JP | 2004-49921 | 2/2004 | |
| JP | 2006-150072 | 6/2006 | |
| JP | WO-2012111438 A1 * | 8/2012 | ........... A61L 27/227 |
| JP | 2013-176547 | 9/2013 | |
| JP | 2013-208425 | 10/2013 | |
| WO | 95/23611 | 9/1995 | |
| WO | 2012/111438 | 8/2012 | |

OTHER PUBLICATIONS

Hart and Gehrke "Thermally Associating Polypeptides Designed for Drug Delivery Produced by Genetically Engineered Cells" J. Pharm. Sci. 96:484-516. (Year: 2006).*

Qiu et al., "Wet-Spinning of Recombinant Silk-Elastin-Like Protein Polymer Fibers with High Tensile Strength and High Deformability", Biomacromolecules, vol. 10, 2009, pp. 602-608.

Sreerama et al., "Estimation of Protein Secondary Structure from Circular Dichroism Spectra: Comparison of CONTIN, SELCON, and CDSSTR Methods with an Expanded Reference Set", Analytical Biochemistry, vol. 287, 2000, pp. 252-260.

Written Opinion of the International Searching Authority dated May 20, 2014, issued for PCT/JP2014/054026.

The Chemical Society of Japan, Shin Jikken Kagaku Koza 20 Seibutsu Kagaku I, pp. 14-19, 26-31, 54-57.

* cited by examiner

*Primary Examiner* — Christina Bradley
*Assistant Examiner* — Zachary J Miknis
(74) *Attorney, Agent, or Firm* — Wenderoth, Lind & Ponack, L.L.P.

(57) ABSTRACT

The present invention aims to provide a wound healing agent that inhibits bacterial growth, promotes granulation tissue formation and epithelization, and minimizes foreign body reaction in the granulation tissue. The wound healing agent of the present invention contains protein (A) and water, wherein the protein (A) contains: GAGAGS (1); and an amino acid sequence (X) and/or an amino acid sequence (X'), and the total percentage of β turns and random coils in the protein (A) as determined by circular dichroism spectroscopy is 60 to 85%, and the percentage of the total number of amino acid residues in the amino acid sequences (X) and (X') is 50 to 70% of the total number of amino acid residues in the protein (A). Amino acid sequence (X): at least one amino acid sequence selected from the group consisting of VPGVG (2), GVGVP (3), and GAHGPAGPK (4). Amino acid sequence (X'): an amino acid sequence in which 1 or 2 amino acid residues in the amino acid sequence (X) are independently replaced by a lysine (K) or arginine (R) residue.

3 Claims, No Drawings

Specification includes a Sequence Listing.

WOUND HEALING AGENT

TECHNICAL FIELD

The present invention relates to a wound healing agent.

BACKGROUND ART

Healing of wounds (such as burn wounds, donor sites, incisional wounds, traumatic skin defects, decubitus skin ulcers, and diabetic skin ulcers) requires an environment that adequately keeps wound areas moist and that promotes cell growth. Thus, gauze, cotton wool, and the like have been used as wound dressings to be applied to affected areas. These dressings rapidly absorb exudate but unfortunately easily cause bacterial infection. Additionally, if the surface of wounds becomes dry, these dressings may cause pain or bleeding at the time of removal. A wound dressing may be used with an ointment or the like in order to prevent the surface of wounds from drying out. Yet, it results in insufficient absorption of exudate, and the surface of wounds may be kept too moist.

In addition, wound dressings such as carboxymethyl cellulose (CMC) gel (Patent Literature 1), which are intended to maintain a moist environment, may be used instead of gauze, cotton wool, ointments, and the like in order to maintain an adequate moist environment. Unfortunately, however, the CMC gel fails to sufficiently maintain the gel structure due to exudate and the like, and may be separated from the wound area or may create a hotbed for bacterial infection.

Meanwhile, a collagen sponge (Patent Literature 2) is known as a wound healing agent that not only maintains a moist environment but also promotes granulation tissue formation and epithelization. While the collagen sponges characteristically have good biocompatibility, they are unfortunately poor at maintaining a moist environment, easily cause bacterial infection and bacterial growth, and undergo degradation by exudate; and materials thereof are not easily available.

In addition, use of a conventional wound healing agent may cause a foreign body reaction (one of biophylactic reactions) which delays the transition to the inflammation phase in the course of wound healing process, resulting in delayed wound healing. Thus, there is a demand for a wound healing agent that minimizes foreign body associated with the wound healing agent.

CITATION LIST

Patent Literature

Patent Literature 1: JP-A H06-009373
Patent Literature 2: JP-A H10-080438

SUMMARY OF INVENTION

Technical Problem

The present invention aims to provide a wound healing agent that inhibits bacterial growth, promotes granulation tissue formation and epithelization, and minimizes foreign body reaction.

Solution to Problem

A wound healing agent of the present invention contains protein (A) and water, wherein the protein (A) contains: GAGAGS (SEQ ID NO:1); and an amino acid sequence (X) and/or an amino acid sequence (X'), the total percentage of β turns and random coils in the protein (A) as determined by circular dichroism spectroscopy is 60 to 85%, and the percentage of the total number of amino acid residues in the amino acid sequences (X) and (X') is 50 to 70% of the total number of amino acid residues in the protein (A).
Amino acid sequence (X): at least one amino acid sequence selected from the group consisting of VPGVG (SEQ ID NO:2), GVGVP (SEQ ID NO:3), and GAHGPAGPK (SEQ ID NO:4).
Amino acid sequence (X'): an amino acid sequence in which 1 or 2 amino acid residues in the amino acid sequence (X) are independently replaced by a lysine (K) or arginine (R) residue.

Advantageous Effects of Invention

The wound healing agent of the present invention inhibits bacterial growth, excels in promoting granulation tissue formation and epithelization, and minimizes foreign body reaction.

DESCRIPTION OF EMBODIMENTS

In the present invention, the protein (A) can be obtained by the following methods: extraction from natural products, organic synthesis (e.g. enzymatic synthesis, solid-phase peptide synthesis, and liquid-phase synthesis), genetic recombination, and the like. Examples of the organic synthesis include methods described in "Seikagaku Jikken Koza 1 (Biochemistry Experimental Course 1), Chemistry of protein IV (edited by Japan Society for Biochemistry, published by Tokyo Kagakudojin on Jul. 1, 1981)" or "Zoku Seikagaku Jikken Koza 2) (Sequel to Biochemistry Experimental Course 2, Chemistry of protein (Vol. 2) (edited by Japan Society for Biochemistry, published by Tokyo Kagakudojin on May 20, 1987)". Examples of the genetic recombination include the method disclosed in Japanese Patent No. 3338441. The protein (A) can be obtained by extraction from natural products, organic synthesis, or genetic recombination. Yet, the genetic recombination is preferred for easy alteration of amino acid sequences and mass productivity at low cost.

The wound healing agent of the present invention contains protein (A) and water, wherein the protein (A) contains: GAGAGS (SEQ ID NO:1); and an amino acid sequence (X) and/or an amino acid sequence (X'), the total percentage of β turns and random coils in the protein (A) as determined by circular dichroism spectroscopy is 60 to 85%, and the percentage of the total number of amino acid residues in the amino acid sequences (X) and (X') is 50 to 70% of the total number of amino acid residues in the protein (A).
Amino acid sequence (X): at least one amino acid sequence selected from the group consisting of VPGVG (SEQ ID NO:2), GVGVP (SEQ ID NO:3), and GAHGPAGPK (SEQ ID NO:4).
Amino acid sequence (X'): an amino acid sequence in which 1 or 2 amino acid residues in the amino acid sequence (X) are independently replaced by a lysine (K) or arginine (R) residue.

In the present invention, the total percentage of β turns and random coils in the protein (A) is in the above range. This allows the amino acid sequence (X) and/or the amino acid sequence (X') in the protein (A) to efficiently interact with cells, resulting in an wound healing agent excellent in forming granulation tissue and promoting epithelization. This also allows the gel structure to be maintained for a long period of time. In addition, the total percentage of β turns and random coils in the protein (A) is in the above range, and the percentage of the total number of amino acid residues in the amino acid sequences (X) and (X') relative to the total number of amino acid residues in the protein (A) is in the above range. This minimizes foreign body reaction associated with the wound healing agent. In addition, the wound healing agent of the present invention is transformed into a gel, for example, after passage of time or when exposed to stimulants such as heat. Thus, gelation occurs upon application of the wound healing agent to a wound, and the wound area can be hermetically sealed with the gel, thus inhibiting bacterial growth. The gelled product can also maintain a moist environment and promote cell growth.

The protein (A) of the present invention has a total percentage of β turns and random coils of 60 to 85% as determined by circular dichroism spectroscopy. Usually, even if two proteins have the same sequence, the total percentage of β turns and random coils is different between these proteins, depending on factors such as method for preparing protein, method for purifying protein, and pH and polarity of a solvent used to dissolve protein.

The total percentage of β turns and random coils in the protein (A) is preferably 60 to 85%, more preferably 65 to 80%, particularly preferably 70 to 75%, for easy interaction with cells (hereinafter referred to as "cellular affinity") and minimization of foreign body reaction.

The percentage can be increased by refolding the protein (A) by techniques such as ammonium sulfate precipitation, ultrafiltration, affinity chromatography, anion exchange chromatography, or the like. The percentage can also be decreased by denaturing the protein (A) with a denaturant, heat, or the like.

The total percentage of β turns and random coils in the protein (A) is determined by the following measurement method.

<Method for Determining the Total Percentage of β Turns and Random Coils in Protein>

Protein is dissolved in deionized water (4° C.) to a concentration of 0.3 mg/ml to prepare an aqueous protein solution. The aqueous protein solution is measured with a circular dichroism spectrometer (J-820, JASCO Corporation) (measurement temperature: 4° C.). The percentage of β turns and the percentage of random coils are calculated using a secondary structure analysis program (JWSSE-480, JASCO Corporation), and these values are added to obtain the total percentage of β turns and random coils.

In the present invention, the protein (A) contains an amino acid sequence (X) and/or an amino acid sequence (X').

Amino acid sequence (X): at least one amino acid sequence selected from the group consisting of VPGVG (SEQ ID NO:2), GVGVP (SEQ ID NO:3), and GAHGPAGPK (SEQ ID NO:4).

Amino acid sequence (X'): an amino acid sequence in which 1 or 2 amino acid residues in the amino acid sequence (X) are independently replaced by a lysine (K) or arginine (R) residue.

The protein (A) may contain multiple units of the amino acid sequence (X) and multiple units of the amino acid sequence (X'). If the protein (A) contains multiple units of the amino acid sequence (X), the amino acid sequence (X) is not limited to one type. If the protein (A) contains multiple units of the amino acid sequence (X'), the amino acid sequence (X') is not limited to one type. Further, the protein (A) may contain both of the amino acid sequence (X) and the amino acid sequence (X').

VPGVG (2) and/or GVGVP (SEQ ID NO:3) are preferred as the amino acid sequence (X) for cellular affinity, minimization of foreign body reaction, and gelation of the protein (A).

Specific examples of the amino acid sequence (X') include GKGVP (SEQ ID NO:7), GKGKP (SEQ ID NO:8), GKGRP (SEQ ID NO:9), and GRGRP (SEQ ID NO:10).

For cellular affinity and gelation of the protein (A), the amino acid sequence (X') is preferably at least one sequence selected from the group consisting of GKGVP (SEQ ID NO:7), GKGKP (SEQ ID NO:8), and GRGRP (SEQ ID NO:10), with GKGVP (SEQ ID NO:7) and/or GKGKP (SEQ ID NO:8) being more preferred.

For cellular affinity, minimization of foreign body reaction, and gelation of the protein (A), the protein (A) preferably contains a polypeptide chain (Y) and/or a polypeptide chain (Y') described below. The polypeptide chain (Y) consists of 2 to 200 tandem repeats of at least one amino acid sequence (X).

Polypeptide chain (Y'): a polypeptide chain in which 0.1 to 20% of the total number of amino acid residues in the polypeptide chain (Y) are independently replaced by a lysine (K) or arginine (R) residue.

Specifically, the polypeptide chain (Y) is (VPGVG(SEQ ID NO:2))$_b$, (GVGVP(SEQ ID NO:3))$_c$, or (GAHGPAGPK (SEQ ID NO:2))$_d$. (Note that b to d each indicate the number of tandem repeats of the amino acid sequence (X), and the number is an integer of 2 to 200.)

If the protein (A) contains multiple polypeptide chains (Y) in one molecule, the protein (A) may contain one or more selected from the group consisting of (VPGVG(SEQ ID NO:2))$_b$, (GVGVP(SEQ ID NO:3))$_c$, and (GAHGPAG-PK(SEQ ID NO:4))$_d$.

In addition, if the protein (A) contains multiple polypeptide chains (Y), the number of repeats of the amino acid sequence (X) may be the same or different between each polypeptide chain (Y). In other words, the protein (A) may contain multiple polypeptide chains (Y) in which the numbers b to d of tandem repeats of the amino acid sequence (X) are the same or different between each polypeptide chain (Y).

(VPGVG(SEQ ID NO:2))$_b$ and/or (GVGVP(SEQ ID NO:3))$_c$ are preferred as the polypeptide chain (Y) for cellular affinity, minimization of foreign body reaction, and an adequate total percentage of β turns and random coils in the protein (A).

The polypeptide chain (Y) is a polypeptide chain consisting of 2 to 200 (the numbers b to d are 2 to 200) tandem repeats of the amino acid sequence (X). The number of tandem repeats of the amino acid sequence (X) is preferably 2 to 100 (the numbers b to d are 2 to 100), more preferably 2 to 50 (the numbers b to d are 2 to 50), particularly preferably 2 to 40 (the numbers b to d are 2 to 40), for cellular affinity, minimization of foreign body reaction, gelation of the protein (A), and an adequate total percentage of β turns and random coils in the protein (A).

In addition, the polypeptide chain (Y') is a polypeptide chain in which 0.1 to 20% of the total number of amino acid residues in the polypeptide chain (Y) are independently replaced by a lysine (K) or arginine (R) residue. Specific examples include a polypeptide chain in which some or all of the repeats of the amino acid sequence (X) in the polypeptide chain (Y) consisting of tandem repeats of the amino acid sequence (X) are replaced by the amino acid sequence (X').

In the polypeptide chain (Y'), the total percentage of amino acid residues replaced by lysine (K) and arginine (R) residues is preferably 0.5 to 10%, more preferably 1 to 5% of the total number of amino acid residues in the polypeptide chain (Y), for solubility of the protein (A) in water, cellular affinity, minimization of foreign body reaction, and an adequate total percentage of β turns and random coils in the protein (A).

The polypeptide chain (Y') can be identified based on whether the polypeptide chain (Y) is obtained when all of lysine (K) and arginine (R) residues in the sequence of the protein (A) are replaced by other amino acid residues (G, A, V, P, H, or K).

The total number of the polypeptide chains (Y) and (Y') in the protein (A) is preferably 1 to 100, more preferably 1 to 80, particularly preferably 1 to 60, for solubility of the protein (A) in water, cellular affinity, minimization of foreign body reaction, and an adequate total percentage of β turns and random coils in the protein (A).

If the protein (A) contains polypeptide chains (Y) each having a different amino acid sequence (X) and/or a different number of tandem repeats of the amino acid sequence (X), each polypeptide chain is counted as one, and the sum of the counts is the number of the polypeptide chains (Y). The same applies to the polypeptide chain (Y').

In the present invention, the protein (A) is one in which the percentage of the total number of amino acid residues in the amino acid sequences (X) and (X') is 50 to 70% of the total number of amino acid residues in the protein (A). The percentage is preferably 52.5 to 67.5%, more preferably 55 to 65%, for cellular affinity and minimization of foreign body reaction.

The percentage of the total number of amino acid residues in the amino acid sequences (X) and (X') relative to the total number of amino acid residues in the protein (A) can be determined with a protein sequencer. Specifically, the percentage can be determined by the following measurement method.

<Method for Determining the Percentage of the Total Number of Amino Acid Residues in the Amino Acid Sequences (X) and (X') Relative to the Total Number of Amino Acid Residues in the Protein (A)>

The protein (A) is divided into fragments of about 30 residues or less using at least two methods for cleaving the sequence at a specific amino acid residue. Subsequently, the fragments are separated by high performance liquid chromatography (HPLC), and then the amino acid sequence is analyzed with a protein sequencer. The entire sequence of the protein (A) is determined by peptide mapping of the amino acid sequences obtained. Subsequently, the total percentage of the number of amino acid residues in the amino acid sequences (X) and (X') is calculated according to the following equation.

Total percentage (%) of the number of amino acid residues in the amino acid sequences (X) and (X')=[{Number of units of the amino acid sequence (X)}×{Number of amino acid residues in the amino acid sequence (X)}+{Number of units of the amino acid sequence (X')}×{Number of amino acid residues in the amino acid sequence (X')}]/{Total number of amino acid residues in the protein (A)}×100

If the protein (A) contains multiple amino acid sequences (X), the "{Number of units of the amino acid sequence (X)}×{Number of amino acid residues in the amino acid sequence (X)}" is determined in the following manner.

First, the "Number of units of the amino acid sequence (X)×Number of amino acid residues in the amino acid sequence (X)" is determined for each amino acid sequence (X). The sum is regarded as a value of "{Number of units of the amino acid sequence (X)}×{Number of amino acid residues in the amino acid sequence (X)}" in the above equation.

The "{Number of units of the amino acid sequence (X')}×{Number of amino acid residues in the amino acid (X')}" in the above equation is determined in the same manner in the case where the protein (A) contains multiple amino acid sequences (X') corresponding to multiple amino acid sequences (X).

In the protein (A), the percentage of the number of amino acid residues in GAGAGS (SEQ ID NO:1) relative to the total number of amino acid residues [{Number of units of GAGAGS (SEQ ID NO:1) in the protein (A)×6}/{Total number of amino acid residues in the protein (A)}×100] is preferably 5 to 50%, more preferably 10 to 47.5%, particularly preferably 20 to 45%, for an adequate total percentage of β turns and random coils, cellular affinity, and minimization of foreign body reaction.

The percentage of the number of amino acid residues in GAGAGS (SEQ ID NO:1) relative to the total number of amino acid residues in the protein (A) can be determined with a protein sequencer. Specifically, the percentage is determined by the following measurement method.

<Percentage of the Number of Amino Acid Residues in GAGAGS (SEQ ID NO:1)>

The protein (A) is divided into fragments of about 30 residues or less using at least two methods for cleaving the sequence at a specific amino acid residue. Subsequently, the fragments are separated by high performance liquid chromatography (HPLC), and then the amino acid sequence is analyzed with a protein sequencer. The entire sequence of the protein (A) is determined by peptide mapping of the amino acid sequences obtained. Subsequently, the percentage of the number of amino acid residues in GAGAGS (SEQ ID NO:1) is calculated according to the following equation.

Percentage (%) of amino acid residues in GAGAGS (SEQ ID NO:1)={Number of units of GAGAGS (SEQ ID NO:1)×6}/{Total number of amino acid residues in the protein (A)}×100

The protein (A) contains GAGAGS (SEQ ID NO:1). Preferably, the protein (A) contains a polypeptide chain (S) consisting of 2 to 200 tandem repeats of GAGAGS (SEQ ID NO:1) for an adequate total percentage of β turns and random coils in the protein (A), cellular affinity, and minimization of foreign body reaction.

In the polypeptide chain (S), the number of tandem repeats of GAGAGS (SEQ ID NO:1) is preferably 2 to 100, more preferably 2 to 50, particularly preferably 2 to 10, for an adequate proportion of β sheets.

If the protein (A) contains a total of two or more of at least one sequence selected from the group consisting of the amino acid sequence (X), the amino acid sequence (X'), the polypeptide chain (Y), the polypeptide chain (Y'), GAGAGS (SEQ ID NO:1), and the polypeptide chain (S), an intervening amino acid sequence (Z) may be present between these sequences. The intervening amino acid sequence (Z) is a peptide sequence consisting of one amino acid residue or two or more amino acid residues linked, and it is none of the following: GAGAGS (SEQ ID NO:1), the amino acid sequence (X), and the amino acid sequence (X'). The number of amino acid residues constituting the intervening amino acid sequence (Z) is preferably 1 to 30, more preferably 1 to 15, particularly preferably 1 to 10, for an adequate total percentage of β turns and random coils in the protein (A). Specific examples of the intervening amino acid sequence (Z) include VAAGY (SEQ ID NO:11), GAAGY (SEQ ID NO:12), and LGP.

The percentage of amino acid residues in the intervening amino acid sequence (Z) relative to the total number of amino acid residues in the protein (A) [Σ{(Number of amino acid residues in the intervening amino acid sequence (Z))× (Number of units of the intervening amino acid sequence (Z))}/{Total number of amino acid residues in the protein (A)}×100] is preferably 0 to 25%, more preferably 0 to 22.5%, particularly preferably 0 to 15%, for an adequate total percentage of β turns and random coils in the protein (A).

The protein (A) may contain a terminal amino acid sequence (T) at each end, in addition to GAGAGS (SEQ ID NO:1), the amino acid sequence (X), the amino acid sequence (X'), and the intervening amino acid sequence (Z). For improvement in the solubility of the protein (A) in water, the terminal structure at each end of the protein (A) is preferably one in which the terminal amino acid sequence (T) is linked to the polypeptide chain (Y) or (Y'). The terminal amino acid sequence (T) is a peptide sequence consisting of one amino acid residue or two or more amino acid residues linked, and it is none of the following: GAGAGS (SEQ ID NO:1), the amino acid sequence (X), and the amino acid sequence (X'). The number of amino acid residues constituting the terminal amino acid sequence (T) is preferably 1 to 100, more preferably 1 to 50, particularly preferably 1 to 40, for cellular affinity and an adequate total percentage of β turns and random coils in the protein (A). Specific examples of the terminal amino acid sequence (T) include MDPVVLQRRDWENPGVTQLNRLAAHPPFAS-DPM (SEQ ID NO:13).

The percentage of the number of amino acid residues in the terminal amino acid sequence (T) relative to the total number of amino acid residues in the protein (A) is preferably 0 to 25%, more preferably 0 to 22.5%, particularly preferably 0 to 15%, for cellular affinity and an adequate total percentage of β turns and random coils in the protein (A).

The protein (A) may be prepared from bacteria using biotechnological techniques. In such a case, the protein (A) may contain, in addition to the terminal amino acid sequence (T), a specific amino acid sequence (hereinafter referred to as "purification tag") at the N or C terminal of the protein (A) in order to facilitate purification or detection of the protein (A). An affinity purification tag is used as the purification tag. Examples of the purification tag include 6×His tag consisting of polyhistidine, V5 tag, Xpress tag, AU1 tag, T7 tag, VSV-G tag, DDDDK tag, S tag, Cruz-Tag09™, CruzTag22™, CruzTag41™, Glu-Glu tag, Ha.11 tag, and KT3 tag.

Examples of combinations of a purification tag (i) and a ligand (ii) capable of recognizing and binding to the tag are listed below.
(i-1) Glutashione-S-transferase (GTS), (ii-1) Glutashione
(i-2) Maltose binding protein (MBP), (ii-2) Amylose
(i-3) HQ tag, (ii-3) Nickel
(i-4) Myc tag, (ii-4) Anti-Myc antibody
(i-5) HA tag, (ii-5) Anti-HA antibody
(i-6) FLAG tag, (ii-6) Anti-FLAG antibody
(i-7) 6×His tag, (ii-7) Nickel or cobalt The purification tag sequence can be added by, for example, incorporating a nucleic acid encoding the purification tag into the 5' or 3' end of the nucleic acid encoding the protein (A) in an expression vector, or using a commercial vector designed to add the purification tag.

The total percentage of amino acid residues in the intervening amino acid sequence (Z), the terminal amino acid sequence (T), and the purification tag is preferably 0 to 25%, more preferably 0 to 22.5%, particularly preferably 0 to 15% of the total number of amino acid residues in the protein (A), for cellular affinity and an adequate total percentage of β turns and random coils in the protein (A).

If the protein (A) contains the polypeptide chain (Y) and/or the polypeptide chain (Y') as well as GAGAGS (SEQ ID NO:1) and/or the polypeptide chain (S), the polypeptide chain (Y) or (Y') is preferably alternately linked with GAGAGS (SEQ ID NO:1) or the polypeptide chain (S) via a chemical bond, for cellular affinity and an adequate total percentage of β turns and random coils in the protein (A).

The ratio of the number of units of GAGAGS (SEQ ID NO:1) to the number of units of the amino acid sequences (X) and (X') [GAGAGS (SEQ ID NO:1):{amino acid sequences (X) and (X')}] is preferably 1:2 to 1:6, more preferably 1:2 to 1:5, for an adequate total percentage of β turns and random coils in the protein (A).

The molecular mass of the protein (A) as determined by SDS-PAGE (SDS polyacrylamide gel electrophoresis) is preferably 15 to 200 kDa, more preferably 30 to 150 kDa, particularly preferably 70 to 120 kDa, for cellular affinity and an adequate total percentage of β turns and random coils in the protein (A).

Some of preferred examples of the protein (A) are listed below.
(A1) A protein in which the amino acid sequence (X) is GVGVP (SEQ ID NO:3)
(A11) A protein containing: a polypeptide chain (Y'1) in which amino acid residues in the polypeptide chain (Y1) consisting of 2 to 200 tandem repeats of GVGVP (SEQ ID NO:3) are individually replaced by a lysine (K) residue; and a polypeptide chain (S1) consisting of 2 to 200 tandem repeats of GAGAGS (SEQ ID NO:1)
(A11-1) A protein containing: a polypeptide chain (Y'11) of (GVGVP)$_4$GKGVP(GVGVP)$_3$ (SEQ ID NO:6) in which one of valine (V) residues in a polypeptide chain (Y11) (GVGVP)$_8$ (SEQ ID NO:17) consisting of 8 tandem repeats of GVGVP (3) is replaced by a lysine (K) residue; and the polypeptide chain (S1) consisting of 2 to 200 tandem repeats of GAGAGS (SEQ ID NO:1)
(A11-1-1) A protein containing: (GAGAGS)$_4$ (SEQ ID NO:5) consisting of 4 tandem repeats of GAGAGS (SEQ ID NO:1); and (GVGVP)$_4$GKGVP(GVGVP)$_3$ (SEQ ID NO:6)

Specific examples of protein (A11-1-1) include the following proteins.
(i) A protein (SELP3) of sequence (18) having a molecular mass of about 30 kDa, consisting of 4 repeats of (GAGAGS)$_4$ (SEQ ID NO:5) and 4 repeats of (GVGVP)$_4$GKGVP(GVGVP)$_3$ (SEQ ID NO:6) in which these sequences are alternately linked by a chemical bond
(ii) A protein of sequence (19) having a molecular mass of about 180 kDa, consisting of 30 repeats of (GAGAGS)$_4$ (SEQ ID NO:5) and 30 repeats of (GVGVP)$_4$GKGVP (GVGVP)$_3$ (SEQ ID NO:6) in which these sequences are alternately linked by a chemical bond
(iii) A protein (SELP8K) of sequence (27) having a molecular mass of about 80 kDa, consisting of 13 repeats of (GAGAGS)$_4$ (SEQ ID NO:5) and 13 repeats of (GVGVP)$_4$ GKGVP(GVGVP)$_3$ (SEQ ID NO:6) in which these sequences are alternately linked by a chemical bond (A11-1-2) A protein containing: (GAGAGS)$_2$ (SEQ ID NO:14) consisting of 2 tandem repeats of GAGAGS (SEQ ID NO:1); and (GVGVP)$_4$GKGVP(GVGVP)$_3$ (SEQ ID NO:6)

Specific examples of protein (A11-1-2) include the following proteins.
(i) A protein (SELPOK) of sequence (15) having a molecular mass of about 82 kDa, consisting of 17 repeats of (GAGAGS)$_2$ (SEQ ID NO:14) and 17 repeats of (GVGVP)$_4$GKGVP(GVGVP)$_3$ (SEQ ID NO:6) in which these sequences are alternately linked by a chemical bond
(A11-1-3) A protein containing: (GAGAGS)$_6$ (SEQ ID NO:22) consisting of 6 tandem repeats of GAGAGS (SEQ ID NO:1); and (GVGVP)$_4$GKGVP(GVGVP)$_3$ (SEQ ID NO:6)

Specific examples of protein (A11-1-3) include the following proteins.
(i) A protein of sequence (24) having a molecular mass of about 110 kDa, consisting of 15 repeats of (GAGAGS)$_6$ (SEQ ID NO:22) and 15 repeats of (GVGVP)$_4$GKGVP(GVGVP)$_3$ (SEQ ID NO:6) in which these sequences are alternately linked by a chemical bond
(A11-2) A protein containing: a polypeptide chain (Y'12) of (GVGVP)$_6$GKGVP(GVGVP)$_5$ (SEQ ID NO:21) in which one amino acid residue in a polypeptide chain consisting of 12 tandem repeats of GVGVP (3) is replaced by a K residue; and the polypeptide chain (S1) consisting of 2 to 200 tandem repeats of GAGAGS (SEQ ID NO:1)
(A11-2-1) A protein containing: (GAGAGS)$_4$ (SEQ ID NO:5) consisting of 4 tandem repeats of GAGAGS (SEQ ID NO:1); and (GVGVP)$_6$GKGVP(GVGVP)$_5$ (SEQ ID NO:21)

Specific examples of protein (A11-2-1) include the following proteins.
(i) A protein of sequence (25) having a molecular mass of about 105 kDa, consisting of 13 repeats of (GAGAGS)$_4$ (SEQ ID NO:5) and 13 repeats of (GVGVP)$_6$GKGVP(GVGVP)$_5$ (SEQ ID NO:21) in which these sequences are alternately linked by a chemical bond
(A12) A protein containing: the polypeptide chain (Y1) consisting of 2 to 200 tandem repeats of GVGVP (SEQ ID NO:3); and the polypeptide chain (51) consisting of 2 to 200 tandem repeats of GAGAGS (SEQ ID NO:1)

Specific examples of protein (A12) include the following proteins.
(i) Protein (SELP6.1) of sequence (31) having a molecular mass of about 110 kDa, consisting of 5 repeats of (GAGAGS)$_8$ (SEQ ID NO:16) and 5 repeats of (GVGVP)$_{40}$ (SEQ ID NO:23) in which these sequences are alternately linked by a chemical bond
(A2) A protein in which the amino acid sequence (X) is VPGVG (SEQ ID NO:2)
(A21) A protein containing: a polypeptide chain (Y2) consisting of 2 to 200 tandem repeats of VPGVG (SEQ ID NO:2); and GAGAGS (SEQ ID NO:1)

The wound healing agent of the present invention contains the protein (A) and water.

The protein (A) content (% by weight) in the wound healing agent is preferably 5 to 30% by weight, more preferably 10 to 30% by weight, particularly preferably 15 to 30% by weight relative to the weight of the wound healing agent, for solubility of the protein (A) in water, gelation of the protein (A), and easy application to the wound area.

The water content (% by weight) in the wound healing agent is preferably 70 to 95% by weight, more preferably 70 to 90% by weight, and particularly preferably 70 to 85% by weight relative to the weight of the wound healing agent, for solubility of the protein (A) in water, gelation of the protein (A), and easy application to the wound area.

The water in the wound healing agent is not particularly limited as long as the water is sterilized. Examples of sterile water include water filtered through a microfiltration membrane having a pore diameter of 0.2 µm or less, water filtered through an ultrafiltration membrane, water treated with a reverse osmosis membrane, and deionized water sterilized by heating in an autoclave at 121° C. for 20 minutes.

The wound healing agent of the present invention may contain an inorganic salt and/or phosphoric acid (salt) in addition to the protein (A) and water.

Specific examples of inorganic salts include sodium chloride, potassium chloride, calcium chloride, magnesium chloride, sodium sulfate, potassium sulfate, calcium sulfate, magnesium sulfate, sodium hydrogen carbonate, potassium hydrogen carbonate, calcium hydrogen carbonate, and magnesium hydrogen carbonate. Herein, the inorganic salt does not include phosphoric acid salts.

For making the wound healing agent isotonic with the body fluids, the inorganic salt content (% by weight) in the wound healing agent is preferably 0.5 to 1.3% by weight, more preferably 0.7 to 1.1% by weight, particularly preferably 0.85 to 0.95% by weight relative to the weight of the wound healing agent.

The term "phosphoric acid (salt)" refers to phosphoric acid and/or phosphoric acid salts.

Examples of the phosphoric acid (salt) include phosphoric acid and phosphoric acid salts.

Examples of phosphoric acid salts include alkali metal salts and alkaline-earth metal salts. Specific examples thereof include sodium salt, potassium salt, calcium salt, and magnesium salt.

For wound healing, the phosphoric acid (salt) content (% by weight) in the wound healing agent is preferably 0.10 to 0.30% by weight, more preferably 0.12 to 0.28% by weight, particularly preferably 0.14 to 0.26% by weight relative to the weight of the wound healing agent.

The pH of the wound healing agent is preferably 5.0 to 9.0, more preferably 6.0 to 8.5, for stability of the protein (A) and wound healing.

If the pH is in the above range, the protein (A) in the wound healing agent will not be denatured, and it makes it possible to achieve an adequate total percentage of β turns and random coils in the protein (A). In addition, the resulting wound healing agent can inhibit bacterial growth, promote granulation tissue formation and epithelization, and minimize foreign body reaction.

The wound healing agent of the present invention can be obtained by mixing various components. The preparation method is not particularly limited. One example is described below.

(Method for Preparing the Wound Healing Agent)

The protein (A) of the present invention and water are mixed at 4° C. to 25° C. to obtain a wound healing agent. An inorganic salt and/or phosphoric acid (salt) may be present in the water, if necessary. Alternatively, an inorganic salt and/or phosphoric acid (salt) may be added to the water, if necessary, after the protein (A) is dissolved in the water.

The wound healing agent is applied to an affected area preferably in such a manner that a defective portion of the affected area is filled with the wound healing agent for inhibition of bacterial growth, promotion of granulation tissue formation and epithelization, and prevention of contractures.

One example of the method for application to an affected area is described below.

(Method for Applying the Wound Healing Agent to an Affected Area)
(1) The wound healing agent is administered to an affected area.
(2) After administration, the affected area is covered with an appropriate dressing to keep the wound healing agent in the affected area.

The material of the dressing used in (2) above is not particularly limited, and examples thereof include polyurethane, silicone, polyvinyl alcohol, polypropylene, polyester, polystyrene, polyethylene, ethylene-vinyl acetate copolymers, and nylon.

The shape of the dressing is not particularly limited as long as the dressing can cover an affected area to keep the wound healing agent in the affected area after the wound healing agent is applied to the affected area. A film dressing is preferred.

The wound healing agent of the present invention is in the form of a solution immediately after mixing of the components such as the protein (A) and water. Yet, for inhibition of bacterial growth, preferably, the wound healing agent becomes less flowable and is transformed into a gel, for example, after passage of time or when exposed to stimulants such as heat.

As for the temperature at which the wound healing agent is transformed into a gel, the wound healing agent is preferably heated at 25° C. to 80° C. for gelation in a short period of time. If the temperature is 80° C. or lower, the wound healing agent is transformed into a gel without reducing the functions of the material for tissue regeneration, and the time required for gelation will be appropriate.

In use of the wound healing agent, the temperature of the wound healing agent at the time of application is preferably 4° C. to 80° C., more preferably 4° C. to 60° C., still more preferably 25° C. to 50° C., particularly preferably 30° C. to 40° C., for thermal stability and handleability of the protein (A).

EXAMPLES

The present invention is described in further detail below with reference to the examples, but the present invention is not limited to these examples.

Preparation Example 1

[Preparation of Protein (A11-1-1(iii)-a)]
Production of SELP8K Protein (A11-1-1(iii))
Plasmid pPT0345 encoding SELP8K was prepared by the method disclosed in EXAMPLES of Japanese Patent No. 4088341.

The plasmid was used to transform E. coli cells into a strain capable of producing SELP8K. The following description is given of a method for producing SELP8K protein (A11-1-1(iii)) of sequence (27), which is one type of the protein (A), using the SELP8K-producing strain.
Culture of SELP8K-Producing Strain A culture solution of the SELP8K-producing strain which had been cultured at 30° C. overnight was inoculated to 50 mL of LB medium in a 250 mL flask. Kanamycin was added to a final concentration of 50 μg/mL, and the culture solution was incubated with agitation (200 rpm) at 30° C. When the turbidity (OD 600) of the inoculated culture solution reached 0.8 (measured with spectrophotometer UV1700, Shimadzu Corporation), 40 mL of the culture solution was transferred to another flask pre-warmed at 42° C. and incubated at the same temperature for about 2 hours. The culture solution was chilled on ice, and the turbidity (OD 600) of the culture solution was measured. E. coli cells were collected by centrifugation.
Purification of SELP8K Protein (A11-1-1(iii))

The collected E. coli cells were used to purify protein from E. coli biomass by the following methods: (1) lysis, (2) removal of insoluble cellular debris by centrifugation, (3) ammonium sulfate precipitation, (4) ultrafiltration, (5) anion exchange chromatography, (6) ultrafiltration, and (7) lyophilization. In this manner, a protein (A11-1-1(iii)-a) having a molecular mass of about 80 kDa, i.e., a purified product of SELP8K protein (A11-1-1(iii)) of sequence (27), was obtained.
(1) Lysis Deionized water (200 g) was added to the collected E. coli cells (100 g), followed by lysis with a high-pressure homogenizer (55 MPa). Thus, a lysate containing lysed cells was obtained. Subsequently, the pH of the lysate was adjusted to 4.0 with glacial acetic acid.
(2) Removal of Insoluble Cellular Debris by Centrifugation The lysate was further centrifuged (6300 rpm, 4° C., 30 min) to collect the supernatant.
(3) Ammonium Sulfate Precipitation A saturated ammonium sulfate solution was added to the collected supernatant to give an ammonium sulfate concentration of 25% by weight, followed by standing for 8 to 12 hours. Then, the precipitate was collected by centrifugation. The collected precipitate was dissolved in deionized water. To the solution was added saturated ammonium sulfate solution to similarly give an ammonium sulfate concentration of 25% by weight, followed by standing for 8 to 12 hours. Then, the precipitate was collected by centrifugation. The collected precipitate was dissolved in deionized water to obtain a solution.
(4) Ultrafiltration The solution obtained in (3) was applied to an ultrafilter with a cut-off molecular weight of 30,000 (Hollow Fiber, GE Healthcare). The solution obtained in (3) was ultrafiltered against deionized water in an amount 10 times the volume of the solution obtained in (3). Thus, the protein was separated by ultrafiltration.
(5) Anion Exchange Chromatography The protein separated by ultrafiltration was dissolved in 10 mM sodium acetate buffer to a concentration of 20 g/L, and applied to AKTA Prime (Amersham) to which an anion exchange column (Hi PrepSPXL16/10, GE Healthcare) was connected. Then, 500 mM sodium acetate buffer was used as an eluent, and the eluted fraction was collected.
(6) Ultrafiltration The solution obtained in (5) was treated in the same manner as in "(4) Ultrafiltration" to separate the protein.
(7) Lyophilization The protein was dissolved in deionized water to give 5 g/L, and the solution was poured into a stainless steel vat in such a manner that the water level would be 15 mm or lower. Subsequently, the solution was placed in a lyophilizer (NIHON TECHNO SERVICE CO., LTD.), and lyophilized at −40° C. over 16 hours. The lyophilized product was subjected to primary drying at a vacuum of 8 Pa or less at −20° C. over 90 hours, and then to secondary drying at a vacuum of 8 Pa or less at 20° C. over 24 hours. Thus, purified protein (A11-1-1(iii)-a) was obtained.
Identification of Protein (A11-1-1(iii)-a)

The obtained protein (A11-1-1(iii)-a) was identified by the following procedures.

The obtained protein (A1-1(iii)-a) was analyzed by Western Blotting using a rabbit anti-SELP8K antibody and a rabbit anti-6×His antibody (Roland Corporation) against 6×His tag at the C terminal. Western Blotting was performed by the procedures described later. A band exhibiting reactivity with each antibody was found at an apparent molecular mass of 80 kDa. The obtained protein was also subjected to amino acid composition analysis, using an amino acid analysis system (Prominence, Shimadzu Corporation). The results revealed that the product was rich in glycine (43.7% by weight), alanine (12.3% by weight), serine (5.3% by weight), proline (11.7% by weight), and valine (21.2% by weight). The product was also found to contain lysine (1.5% by weight). Table 1 below shows a correlation between the composition of the purified product and the predicted theoretical composition determined based on the synthetic gene sequence.

Thus, protein (A11-1-1(iii)-a) was confirmed as SELP8K protein (A11-1-1(iii)) of the sequence (27) consisting of 13 polypeptide chains (Y'11) of (GVGVP)$_4$GKGVP(GVGVP)$_3$ (SEQ ID NO:6) in which one of valine (V) residues in the polypeptide chain (Y) consisting of 8 tandem repeats of GVGVP (SEQ ID NO:3) are replaced by a lysine (K) residue, and 13 polypeptide chains (51) of (GAGAGS)$_4$ (SEQ ID NO:5) consisting of 4 tandem repeats of GAGAGS (SEQ ID NO:1), in which these sequences are alternately linked by a chemical bond.

TABLE 1

| Amino acids | Actual Ratio (%) | Theoretical Ratio (%) |
|---|---|---|
| Ala | 12.3 | 12.2 |
| Asx | 0.9 | 0.8 |
| Glx | n.d. | 0.4 |
| Phe | 0.4 | 0.1 |
| Gly | 43.7 | 41.5 |
| His | 0.4 | 0.8 |
| Ile | 0.3 | 0 |
| Lys | 1.5 | 1.5 |
| Leu | 0.3 | 0.5 |
| Met | 0.3 | 0.3 |
| Pro | 11.7 | 12.4 |
| Arg | 0.5 | 0.6 |
| Ser | 5.3 | 6.1 |
| Thr | n.d. | 0.1 |
| Val | 21.2 | 22.4 |
| Tyr | 1.1 | 0.1 |

<Western Blotting>

Sample for Western Blotting (20 μL) was mixed with 10 μL of 3×SDS treatment buffer (150 mM Tris HCl (pH 6.8), 300 mM dithiothreitol, 6% by weight dodecyl sodium sulfate (SDS), 0.3% by weight bromophenol blue, and 30% by weight glycerol), and heated at 95° C. for 5 minutes. Thus, sample for electrophoresis was prepared. SDS-PAGE was carried out with the sample for electrophoresis (15 μL). After electrophoresis, the gel was transferred to a polyvinylidene fluoride membrane (hereinafter also simply referred to as "membrane"), and immersed in blocking buffer (20 mM Tris (pH 7.6), 137 mM NaCl, 0.1% by weight Tween 20, and 5% skim milk) with shaking at room temperature for 1 hour. Thus, the membrane was blocked. After blocking, the membrane was washed with TBS-T (20 mM Tris (pH 7.6), 137 mM NaCl, and 0.1% by weight Tween 20) for 2 minutes. Next, the membrane was immersed in a solution of primary antibody (a 1:500 dilution of primary antibody (anti-SELP8K antibody or anti-His-tag antibody (Rockland Immunochemicals Inc.) in TBS-T), and left to stand at 4° C. overnight for antibody reaction. After reaction, the membrane was washed 4 times in TBS-T (5 minutes per time) and immersed in a solution of secondary antibody capable of binding to the primary antibody and containing horseradish peroxidase as a marker enzyme (a solution of secondary antibody is a 1:2000 dilution of secondary antibody (ECL anti-rabbit IgG HRP linked F(ab') 2 fragment (GE Healthcare Bio-Sciences)) in TBS-T), and left to stand at room temperature for 30 minutes for antibody reaction. After reaction, the membrane was washed 4 times in TBS-T for (5 minutes per time), and enzyme reaction was carried out using ECL-Advance Western Blotting Detection kit (GE Healthcare Bio-Sciences). A luminometer For ECL (Amersham) was used to expose the membrane to a high speed black and white instant film (Fujifilm Corporation) to visualize bands. When no bands were detectable with the naked eye, SELP8K protein (A11-1-1(iii)-a) was considered to have been disappeared through degradation and absorption.

Measurement of the Total Percentage of β Turns and Random Coils

Protein (A11-1-1(iii)-a) obtained above was used to measure the total percentage of β turns and random coils by the following procedures.

Protein (A1-1) was dissolved in deionized water (4° C.) to a concentration of 0.3 mg/ml to prepare an aqueous solution of protein (A1-1). The aqueous solution of protein (A1-1) was measured with a circular dichroism spectrometer (J-820, JASCO Corporation) (measurement temperature: 4° C.). The total percentage of β turns and the percentage of random coils were calculated using a secondary structure analysis program (JWSSE, JASCO Corporation). Table 2 shows the results.

Preparation Example 2

Protein (A11-1-1(iii)-b) was prepared in the same manner as in "Preparation of protein (A11-1-1(iii)-a)" of Preparation Example 1, except that "(5-2) Refolding (high dilution method)" described below was carried out between "(5) Anion exchange chromatography" and "(6) Ultrafiltration" for "Purification of SELP8K protein (A11-1-1(iii))". Then, the total percentage of β turns and the percentage of random coils were measured. Table 2 shows the results.

(5-2) Refolding (High Dilution Method)

The eluted fraction from anion exchange chromatography was mixed with a 10M urea solution (a protein denaturant) to give a 6M urea solution, followed by standing for 12 hours at 4° C. The prepared solution was transferred to a dialysis membrane (Viskase Companies, Inc.) and dialyzed for 12 hours against deionized water in an amount 10 times the volume of the eluted fraction. Subsequently, the deionized water was discarded and replaced with fresh deionized water in an amount 10 times the volume of the eluted fraction to dialyze for another 12 hours. This operation was repeated 3 more times (a total of 5 times of dialysis) in the above manner. Subsequently, the solution in the dialysis membrane was collected.

Preparation Example 3

Protein (A11-1-1(iii)-c) was prepared in the same manner as in "Preparation of protein (A11-1-1(iii)-a)" of Preparation Example 1, except that "(5-3) Refolding (high dilution method)" described below was carried out between "(5) Anion exchange chromatography" and "(6) Ultrafiltration" for "Purification of SELP8K protein (A11-1-1(iii))". Then, the total percentage of β turns and the percentage of random coils were measured. Table 2 shows the results.

(5-3) Refolding (High Dilution Method)

The eluted fraction from anion exchange chromatography was mixed with a 10M urea solution (a protein denaturant) to give a 6M urea solution, followed by standing for 12 hours at 4° C. The prepared solution was transferred to a dialysis membrane (Viskase Companies, Inc.) and dialyzed for 12 hours against deionized water in an amount 10 times the volume of the eluted fraction. Subsequently, the deionized water was discarded and replaced with fresh deionized water in an amount 3 times the volume of the eluted fraction to dialyze for another 12 hours. This operation was repeated 5 more times (a total of 7 times of dialysis) against deionized water in an amount 3 times the volume of the eluted fraction. Subsequently, the solution in the dialysis membrane was collected.

Preparation Example 4

Protein (A11-1-1(iii)-d) was prepared in the same manner as in "Preparation of protein (A11-1-1(iii)-a)" of Preparation Example 1, except that "(5') Affinity chromatography" described below was carried out instead of "(5) Anion exchange chromatography" for "Purification of SELP8K protein (A11-1-1(iii))". Then, the total percentage of β turns and the percentage of random coils were measured. Table 2 shows the results.

(5') Affinity Chromatography

The protein separated by "(4) Ultrafiltration" was purified by affinity chromatography (Ni Sepharose 6 Fast Flow, GE Healthcare) using His-tag, and the eluted fraction was collected.

Preparation Example 5

Protein (A11-2-1(i)-a) of sequence (25) consisting of 13 repeats of (GAGAGS)$_4$ (SEQ ID NO:5) and 13 repeats of (GVGVP)$_6$GKGVP(GVGVP)$_3$ (SEQ ID NO:21) in which these sequences are alternately linked by a chemical bond was prepared in the same manner as in Preparation Example 1, except that "pPT0345-220 encoding protein (A11-2-1(i)) of sequence (25) having a molecular mass of about 105 kDa" was used instead of "plasmid pPT0345 encoding SELP8K". Then, the total percentage of β turns and random coils was measured. Table 2 shows the results.

Preparation Example 6

Protein (A11-2-1(i)-b) was prepared in the same manner as in Preparation Example 1, except that "pPT0345-220 encoding protein (A11-2-1(i)) of sequence (25) having a molecular mass of about 105 kDa" was used instead of "plasmidpPT0345 encoding SELP8K" and that "(5-2) Refolding (high dilution method)" described above was carried out between "(5) Anion exchange chromatography" and "(6) Ultrafiltration" for "Purification of SELP8K protein (A11-1-1(iii))" in "Preparation of protein (A11-1-1(iii)-a)". Then, the total percentage of β turns and random coils was measured. Table 2 shows the results.

Preparation Example 7

Protein (A11-1-3 (i)-a) of sequence (24) consisting of 15 repeats of (GAGAGS)$_6$ (SEQ ID NO:22) and 15 repeats of (GVGVP)$_4$GKGVP(GVGVP)$_3$ (SEQ ID NO:6) in which these sequences are alternately linked by a chemical bond was prepared in the same manner as in Preparation Example 1, except that "pPT0345-002 encoding protein (A11-1-3(i)) of sequence (24) having a molecular mass of about 110 kDa" was used instead of "plasmidpPT0345 encoding SELP8K". Then, the total percentage of β turns and random coils was measured. Table 2 shows the results.

Preparation Example 8

Protein (A11-2-1(i)-b) was prepared in the same manner as in Preparation Example 1, except that "pPT0345-002 encoding protein (A11-1-3(i)) of sequence (24) having a molecular mass of about 110 kDa" was used instead of "plasmidpPT0345 encoding SELP8K" and that "(5-2) Refolding (high dilution method)" described above was carried out between "(5) Anion exchange chromatography" and "(6) Ultrafiltration" for "Purification of SELP8K protein (A11-1-1(iii))" in "Preparation of protein (A11-1-1(iii)-a)". Then, the total percentage of β turns and random coils was measured. Table 2 shows the results.

Preparation Example 9

Protein (A11-1-1(i)) of sequence (18) consisting of 4 repeats of (GAGAGS)$_4$ (SEQ ID NO:5) and 4 repeats of (GVGVP)$_4$GKGVP(GVGVP)$_3$ (SEQ ID NO:6) in which these sequences are alternately linked by a chemical bond was prepared in the same manner as in Preparation Example 1, except that "pPT0345-004 encoding protein (A11-1-1(i)) of sequence (18) having a molecular mass of about 30 kDa" was used instead of "plasmidpPT0345 encoding SELP8K" and that the ultrafilter was replaced with an ultrafilter with a cut-off molecular mass of 10,000. Then, the total percentage of β turns and random coils was measured. Table 2 shows the results.

Preparation Example 10

Protein (A11-1-1(ii)) of sequence (19) consisting of 30 repeats of (GAGAGS)$_4$ (SEQ ID NO:5) and 30 repeats of (GVGVP)$_4$GKGVP(GVGVP)$_3$ (SEQ ID NO:6) in which these sequences are alternately linked by a chemical bond was prepared in the same manner as in Preparation Example 1, except that "pPT0345-030 encoding protein (A11-1-1(ii)) of sequence (19) having a molecular mass of about 180 kDa" was used instead of "plasmidpPT0345 encoding SELP8K". Then, the total percentage of β turns and random coils was measured. Table 2 shows the results.

Comparative Preparation Example 1

Protein (A11-1-1(iii)-e) was prepared in the same manner as in "Preparation of protein (A11-1-1(iii)-a)" of Preparation Example 1, except that "(5") Affinity chromatography" described below was carried out instead of "(5) Anion exchange chromatography" for "Purification of SELP8K protein (A11-1-1(iii))". Then, the total percentage of β turns and random coils was measured. Table 2 shows the results.

(5") Affinity Chromatography

The protein separated by "(4) Ultrafiltration" was purified by affinity chromatography (TALON (registered trademark) Single Step Columns, Clontech Laboratories, Inc.) using His-tag, and the eluted fraction was collected.

Comparative Preparation Example 2

Protein (A11-1-1(iii)-f) was prepared in the same manner as in "Preparation of protein (A11-1-1(iii)-a)" of Preparation Example 1, except that "(3) Ammonium sulfate precipitation, (4) Ultrafiltration, and (5) Anion exchange chromatography" for "Purification of SELP8K protein (A11-1-1(iii))" were not carried out and that "(5') Affinity chromatography" was carried out. Then, the total percentage of β turns and random coils was measured. Table 2 shows the results.

Comparative Preparation Example 3

Protein (A11-1-1(iii)-g) was prepared in the same manner as in "Preparation of protein (A11-1-1(iii)-a)" of Preparation Example 1, except that "(5) Anion exchange chromatography" for "Purification of SELP8K protein (A11-1-1(iii))" was not carried out. Then, the total percentage of β turns and random coils was measured. Table 2 shows the results.

Comparative Preparation Example 4

Protein (B1) of sequence (28) having a molecular mass of about 37 kDa, consisting of 20 repeats of (VPGVG)$_4$ (SEQ ID NO:26) and 20 repeats of VV in which these sequences are alternately linked by a chemical bond was prepared in the same manner as in Preparation Example 1, except that "plasmid pPT0102-2 encoding ELP1.2" was used instead of "plasmid pPT0345 encoding SELP8K". Then, the total percentage of β turns and random coils was measured. Table 2 shows the results.

Comparative Preparation Example 5

Protein (B2) of sequence (30) having a molecular mass of about 93 kDa, consisting of 29 repeats of (GAGAGS)$_6$ (SEQ ID NO:22) and 29 repeats of (GVGVP)$_2$ (SEQ ID NO:29) in which these sequences are alternately linked by a chemical bond was prepared in the same manner as in Preparation Example 1, except that "pSY1398-1 encoding SLP4.1" was used instead of "plasmid pPT0345 encoding SELP8K". Then, the total percentage of β turns and random coils was measured. Table 2 shows the results.

Comparative Preparation Example 6

Protein (B3) of sequence (20) having a molecular mass of about 17 kDa, consisting of 2 repeats of (GAGAGS)$_4$ (SEQ ID NO:5) and 2 repeats of (GVGVP)$_4$GKGVP(GVGVP)$_3$ (SEQ ID NO:6) in which these sequences are alternately linked by a chemical bond was prepared in the same manner as in Preparation Example 1, except that "pPT0345-102 encoding protein (B3) of sequence (20) having a molecular mass of about 17 kDa" was used instead of "plasmid pPT0345 encoding SELP8K" and that the ultrafilter was replaced with an ultrafilter with a cut-off molecular mass of 10,000. Then, the total percentage of β turns and random coils was measured. Table 2 shows the results.

TABLE 2

| | | Types of protein | Sequences (SEQ ID NO:) | Number of repeats of sequences (left) in protein | Percentage (%) of the number of amino acid residues in GAGAGS (1) | Total percentage (%) of amino acid sequences (X) and (X') | Total percentage (%) of β turns and random coils |
|---|---|---|---|---|---|---|---|
| Preparation Examples | 1 | A11-1-1 (iii)-a | (GVGVP)$_4$GKGVP (GVGVP)$_3$(GAGAGS)$_4$ (27) | 13 | 35.3 | 58.8 | 70.9 |
| | 2 | A11-1-1 (iii)-b | (GVGVP)$_4$GKGVP (GVGVP)$_3$(GAGAGS)$_4$ (27) | 13 | 35.3 | 58.8 | 66.8 |
| | 3 | A11-1-1 (iii)-c | (GVGVP)$_4$GKGVP (GVGVP)$_3$(GAGAGS)$_4$ (27) | 13 | 35.3 | 58.8 | 84.1 |
| | 4 | A11-1-1 (iii)-d | (GVGVP)$_4$GKGVP (GVGVP)$_3$(GAGAGS)$_4$ (27) | 13 | 35.3 | 58.8 | 61.2 |
| | 5 | A11-2-1 (i)-a | (GVGVP)$_6$GKGVP (GVGVP)$_5$(GAGAGS)$_4$ (25) | 13 | 27.3 | 68.1 | 79.7 |
| | 6 | A11-2-1 (i)-b | (GVGVP)$_6$GKGVP (GVGVP)$_5$(GAGAGS)$_4$ (25) | 13 | 27.3 | 68.1 | 68.8 |
| | 7 | A11-1-3 (i)-a | (GVGVP)$_4$GKGVP (GVGVP)$_3$(GAGAGS)$_6$ (24) | 15 | 45.3 | 50.3 | 81.4 |
| | 8 | A11-1-3 (i)-b | (GVGVP)$_4$GKGVP (GVGVP)$_3$(GAGAGS)$_6$ (24) | 15 | 45.3 | 50.3 | 71.2 |
| | 9 | A11-1-1 (i) | (GVGVP)$_4$GKGVP (GVGVP)$_3$(GAGAGS)$_4$ (18) | 4 | 31.2 | 51.9 | 65.9 |
| | 10 | A11-1-1 (ii) | (GVGVP)$_4$GKGVP (GVGVP)$_3$(GAGAGS)$_4$ (18) | 30 | 36.5 | 60.9 | 71.1 |
| Comparative Preparation Examples | 1 | A11-1-1 (iii)-e | (GVGVP)$_4$GKGVP (GVGVP)$_3$(GAGAGS)$_4$ (18) | 13 | 35.3 | 58.8 | 58.1 |
| | 2 | A11-1-1 (iii)-f | (GVGVP)$_4$GKGVP (GVGVP)$_3$(GAGAGS)$_4$ (18) | 13 | 35.3 | 58.8 | 25.5 |
| | 3 | A11-1-1 (iii)-g | (GVGVP)$_4$GKGVP (GVGVP)$_3$(GAGAGS)$_4$ (18) | 13 | 35.3 | 58.8 | 85.6 |

TABLE 2-continued

| | Types of protein | Sequences (SEQ ID NO:) | Number of repeats of sequences (left) in protein | Percentage (%) of the number of amino acid residues in GAGAGS (1) | Total percentage (%) of amino acid sequences (X) and (X') | Total percentage (%) of β turns and random coils |
|---|---|---|---|---|---|---|
| 4 | B1 | (VPGVG)₄VV (28) | 20 | 0.0 | 81.3 | 15.4 |
| 5 | B2 | (GAGAGS)₆(GVGVP)₂ (30) | 29 | 75.3 | 20.9 | 62.4 |
| 6 | B3 | (GVGVP)₄GKGVP (GVGVP)₃(GAGAGS)₄ (30) | 2 | 26.7 | 44.4 | 65.5 |

Example 1

Protein (A11-1-1(iii)-a) was dissolved in 20 mM phosphate buffer (NaCl: 8 g/L, KCl: 0.2 g/L, pH 7.4) to a concentration of 20% by weight. Thus, a wound healing agent (1) was prepared.

Example 2

Protein (A11-1-1(iii)-b) was dissolved in 20 mM phosphate buffer (NaCl: 8 g/L, KCl: 0.2 g/L, pH 7.4) to a concentration of 20% by weight. Thus, a wound healing agent (2) was prepared.

Example 3

Protein (A11-1-1(iii)-c) was dissolved in 20 mM phosphate buffer (NaCl: 8 g/L, KCl: 0.2 g/L, pH 7.4) to a concentration of 20% by weight. Thus, a wound healing agent (3) was prepared.

Example 4

Protein (A11-1-1(iii)-d) was dissolved in 20 mM phosphate buffer (NaCl: 8 g/L, KCl: 0.2 g/L, pH 7.4) to a concentration of 20% by weight. Thus, a wound healing agent (4) was prepared.

Example 5

Protein (A11-2-1(i)-a) was dissolved in 20 mM phosphate buffer (NaCl: 8 g/L, KCl: 0.2 g/L, pH 7.4) to a concentration of 20% by weight. Thus, a wound healing agent (5) was prepared.

Example 6

Protein (A11-2-1(i)-b) was dissolved in 20 mM phosphate buffer (NaCl: 8 g/L, KCl: 0.2 g/L, pH 7.4) to a concentration of 20% by weight. Thus, a wound healing agent (6) was prepared.

Example 7

Protein (A11-1-3 (i)-a) was dissolved in 20 mM phosphate buffer (NaCl: 8 g/L, KCl: 0.2 g/L, pH 7.4) to a concentration of 20% by weight. Thus, a wound healing agent (7) was prepared.

Example 8

Protein (A11-1-3 (i)-b) was dissolved in 20 mM phosphate buffer (NaCl: 8 g/L, KCl: 0.2 g/L, pH 7.4) to a concentration of 20% by weight. Thus, a wound healing agent (8) was prepared.

Example 9

Protein (A11-1-1(i)) was dissolved in 20 mM phosphate buffer (NaCl: 8 g/L, KCl: 0.2 g/L, pH 7.4) to a concentration of 20% by weight. Thus, a wound healing agent (9) was prepared.

Example 10

Protein (A11-1-1(ii)) was dissolved in 20 mM phosphate buffer (NaCl: 8 g/L, KCl: 0.2 g/L, pH 7.4) to a concentration of 20% by weight. Thus, a wound healing agent (10) was prepared.

Comparative Example 1

Protein (A11-1-1(iii)-e) was dissolved in 20 mM phosphate buffer (NaCl: 8 g/L, KCl: 0.2 g/L, pH 7.4) to a concentration of 20% by weight. Thus, a wound healing agent (11) was prepared.

Comparative Example 2

Protein (A11-1-1(iii)-f) was dissolved in 20 mM phosphate buffer (NaCl: 8 g/L, KCl: 0.2 g/L, pH 7.4) to a concentration of 20% by weight. Thus a wound healing agent (12) was prepared.

Comparative Example 3

Protein (A11-1-1(iii)-g) was dissolved in 20 mM phosphate buffer (NaCl: 8 g/L, KCl: 0.2 g/L, pH 7.4) to a concentration of 20% by weight. Thus, a wound healing agent (13) was prepared.

Comparative Example 4

Protein (B1) was dissolved in 20 mM phosphate buffer (NaCl: 8 g/L, KCl: 0.2 g/L, pH 7.4) to a concentration of 20% by weight. Thus, a wound healing agent (14) was prepared.

;Comparative Example 5

Protein (B2) was dissolved in 20 mM phosphate buffer (NaCl: 8 g/L, KCl: 0.2 g/L, pH 7.4) to a concentration of 20% by weight. Thus, a wound healing agent (15) was prepared.

Comparative Example 6

Protein (B3) was dissolved in 20 mM phosphate buffer (NaCl: 8 g/L, KCl: 0.2 g/L, pH 7.4) to a concentration of 20% by weight. Thus, a wound healing agent (16) was prepared.

Evaluation 1

(Evaluation of Gelling Properties of the Protein)
The wound healing agents (1) to (16) were left to stand at 37° C., and the time required for gelation was measured. Gelation was checked by inverting a plastic tube container (Eppendorf tube, 1.5 mL) containing the wound healing agent (100 µL) at intervals of 5 minutes. If the solution did not drip, it was considered that gelation has occurred. If the solution continued to drip or if it took at least 2 hours for gelation, it was considered that gelation did not occur. Table 3 shows the results.

Evaluation 2

(Treatment Test Using Full-Thickness Wound Model in Healthy Guinea Pigs)
Seven-week-age healthy female guinea pigs (std: Hartley) (Japan SLC, Inc.) were anesthetized and depilated. After disinfection, a full-thickness wound (10×10 mm) was formed on the back skin of each guinea pig. In the wounds, the fat layer was completely exposed. After hemostasis and drying, the wound healing agents (1) to (16) were separately applied to the wounds, and a polyurethane film was attached thereto. Subsequently, each wound area was covered with gauze, and the gauze was fixed to the skin around the wound area with a nylon thread. The guinea pigs were sacrificed on day 5 or 10 of the treatment period, and skin samples were taken from the wound areas to prepare pathological specimens (HE stain). Specifically, 11 pathological specimens were prepared for each wound healing agent.

The pathological specimens taken on day 5 of the treatment period were measured for the height of granulation tissue from the panniculus with a microruler. Table 3 shows the evaluation results. It should be noted that each evaluation result is the average of the 11 specimens.

The pathological specimens taken on day 10 of the treatment period were measured for the length of epithelium developed from normal tissue with a microruler. Table 3 shows the evaluation results. It should be noted that each evaluation result is the average of the 11 specimens.

Evaluation 3

(Bacterial Growth Inhibition Test Using Full-Thickness Wound Model in Healthy Guinea Pigs)
Seven-week-age healthy female guinea pigs (std: Hartley) (Japan SLC, Inc.) were anesthetized and depilated. After disinfection, a full-thickness wound (10×10 mm) was formed on the back skin of each guinea pig. In the wounds, the fat layer was completely exposed. After hemostasis and drying, *Pseudomonas aeruginosa* was inoculated at $10^6$ cells per wound area, the wound healing agents (1) to (16) were separately applied to the wounds, and a polyurethane film was attached thereto. Subsequently, each wound area was covered with gauze, and the gauze was fixed to the skin around the wound area with a nylon thread. The guinea pigs were sacrificed on day 3 of the treatment period, and skin samples were taken from the wound areas. Then, the number of bacteria was determined by the bacterial colony method. Table 3 shows the evaluation results.

Evaluation 4

(Scoring of Inflammatory Cell Infiltration Using Full-Thickness Wound Model in Healthy Guinea Pigs)
A total of 13 pathological specimens were prepared for each wound healing agent in the same manner as described above, except that the guinea pigs were sacrificed on day 7 of the treatment period in Evaluation 2. The pathological specimens were evaluated for the percentage of inflammatory cells relative to the number of cells adjacent to the wound healing agents not incorporated into granulation tissue, based on the following 5-point evaluation, and scores were given. Table 3 shows the results. It should be noted that each evaluation result is the average of the 13 specimens. A higher score indicates a greater degree of suppression of infiltration of inflammatory cells induced by the wound healing agent, thus, a higher ability of the wound healing agent to minimize foreign body reaction.

1 point: No formation of granulation tissue in the defective portion.
2 points: Inflammatory cells account for 75% or more of the number of cells adjacent to the wound healing agents not incorporated into granulation tissue.
3 points: Inflammatory cells account for 50% (inclusive) to 75% (exclusive) of the number of cells adjacent to the wound healing agents not incorporated into granulation tissue.
4 points: Inflammatory cells account for 25% (inclusive) to 50% (exclusive) of the number of cells adjacent to the wound healing agents not incorporated into granulation tissue.
5 points: Inflammatory cells account for less than 25% of the number of cells adjacent to the wound healing agents not incorporated into granulation tissue.

TABLE 3

|  |  |  | Wound healing agent | Evaluation 1 Gelation time (min) | Evaluation 2 | | Evaluation 3 | Evaluation 4 |
|---|---|---|---|---|---|---|---|---|
|  |  |  |  |  | Height of granulation tissue (mm) | Length of epithelium (mm) | Number of bacteria ($\times 10^6$) | Score of inflammatory cell infiltration |
| Examples | A11-1-1(iii)-a | 1 | 1 | 115 | 0.68 | 4.3 | 12 | 3.8 |
|  | A11-1-1(iii)-b | 2 | 2 | 90 | 0.78 | 4.2 | 15 | 3.7 |
|  | A11-1-1(iii)-c | 3 | 3 | 115 | 0.64 | 4.2 | 13 | 3.9 |
|  | A11-1-1(iii)-d | 4 | 4 | 75 | 0.63 | 4.2 | 12 | 3.3 |
|  | A11-2-1(i)-a | 5 | 5 | 105 | 0.64 | 4.3 | 10 | 3.5 |

TABLE 3-continued

|  |  | Wound healing agent | Evaluation 1 Gelation time (min) | Evaluation 2 Height of granulation tissue (mm) | Evaluation 2 Length of epithelium (mm) | Evaluation 3 Number of bacteria ($\times 10^6$) | Evaluation 4 Score of inflammatory cell infiltration |
|---|---|---|---|---|---|---|---|
|  | A11-2-1(i)-b | 6 | 6 | 95 | 0.68 | 4.4 | 9 | 3.4 |
|  | A11-1-3(i)-a | 7 | 7 | 115 | 0.64 | 4.1 | 12 | 3.8 |
|  | A11-1-3(i)-b | 8 | 8 | 100 | 0.67 | 4.1 | 11 | 3.4 |
|  | A11-1-1(i) | 9 | 9 | 115 | 0.62 | 4.2 | 5 | 3.6 |
|  | A11-1-1(ii) | 10 | 10 | 70 | 0.79 | 4.9 | 3 | 3.8 |
| Comparative | A11-1-1(iii)-e | 1 | 11 | 85 | 0.54 | 3.1 | 19 | 2.1 |
| Examples | A11-1-1(iii)-f | 2 | 12 | 90 | 0.49 | 2.8 | 21 | 2.0 |
|  | A11-1-1(iii)-g | 3 | 13 | No gelation | 0.33 | 2.2 | 112 | 1.2 |
|  | B1 | 4 | 14 | No gelation | 0.37 | 1.9 | 69 | 1.7 |
|  | B2 | 5 | 15 | 95 | 0.55 | 2.8 | 28 | 2.2 |
|  | B3 | 6 | 16 | 115 | 0.51 | 2.8 | 36 | 2.2 |

The results in table 3 show that the wound healing agent of the present invention is excellent in granulation tissue formation, epithelization, and inhibition of bacterial growth. The results also show that infiltration of inflammatory cells induced by the wound healing agent is suppressed. This indicates that the wound healing agent minimizes foreign body reaction.

INDUSTRIAL APPLICABILITY

The wound healing agent of the present invention is excellent in inhibiting bacterial growth, forming granulation tissue, and promoting epithelization. The wound healing agent also minimizes foreign body reaction. Thus, the present invention is effective as a wound healing agent for healing affected areas resulting from disease or wounds such as burn wounds, donor sites, incisional wounds, and traumatic skin defects.

The invention claimed is:

1. A composition comprising protein (A) and water, wherein the protein (A) contains the amino acid sequence of SEQ ID No: 15, 18, 19, 24, 25, 27 or 31, and the total percentage of β turns and random coils in the protein (A) as determined by circular dichroism spectroscopy is 60 to 85%.

2. The composition according to claim 1, wherein the protein (A) has a molecular mass of 15 to 200 kDa as determined by SDS-PAGE (SDS polyacrylamide gel electrophoresis) method.

3. The composition according to claim 1, wherein the protein (A) content is 5 to 30% by weight and the water content is 70 to 95% by weight relative to the weight of the composition.

* * * * *

```
                        SEQUENCE LISTING

<160> NUMBER OF SEQ ID NOS: 31

<210> SEQ ID NO 1
<211> LENGTH: 6
<212> TYPE: PRT
<213> ORGANISM: artificial sequence
<220> FEATURE:
<223> OTHER INFORMATION: Synthetic construct

<400> SEQUENCE: 1

Gly Ala Gly Ala Gly Ser
1               5

<210> SEQ ID NO 2
<211> LENGTH: 5
<212> TYPE: PRT
<213> ORGANISM: Homo sapiens

<400> SEQUENCE: 2

Val Pro Gly Val Gly
1               5

<210> SEQ ID NO 3
<211> LENGTH: 5
<212> TYPE: PRT
<213> ORGANISM: Homo sapiens

<400> SEQUENCE: 3
```

```
Gly Val Gly Val Pro
1               5

<210> SEQ ID NO 4
<211> LENGTH: 9
<212> TYPE: PRT
<213> ORGANISM: Homo sapiens

<400> SEQUENCE: 4

Gly Ala His Gly Pro Ala Gly Pro Lys
1               5

<210> SEQ ID NO 5
<211> LENGTH: 24
<212> TYPE: PRT
<213> ORGANISM: artificial sequence
<220> FEATURE:
<223> OTHER INFORMATION: Synthetic construct: polypeptide chain(S)

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser
            20

<210> SEQ ID NO 6
<211> LENGTH: 40
<212> TYPE: PRT
<213> ORGANISM: artificial sequence
<220> FEATURE:
<223> OTHER INFORMATION: Synthetic construct: polypeptide chain(Y')

<400> SEQUENCE: 6

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro
        35                  40

<210> SEQ ID NO 7
<211> LENGTH: 5
<212> TYPE: PRT
<213> ORGANISM: artificial sequence
<220> FEATURE:
<223> OTHER INFORMATION: Synthetic construct: amino acid sequence(X')

<400> SEQUENCE: 7

Gly Lys Gly Val Pro
1               5

<210> SEQ ID NO 8
<211> LENGTH: 5
<212> TYPE: PRT
<213> ORGANISM: artificial sequence
<220> FEATURE:
<223> OTHER INFORMATION: Synthetic construct: amino acid sequence(X')

<400> SEQUENCE: 8

Gly Lys Gly Lys Pro
1               5

<210> SEQ ID NO 9
<211> LENGTH: 5
<212> TYPE: PRT
```

```
<213> ORGANISM: artificial sequence
<220> FEATURE:
<223> OTHER INFORMATION: Synthetic construct: amino acid sequence(X')

<400> SEQUENCE: 9

Gly Lys Gly Arg Pro
1               5

<210> SEQ ID NO 10
<211> LENGTH: 5
<212> TYPE: PRT
<213> ORGANISM: artificial sequence
<220> FEATURE:
<223> OTHER INFORMATION: Synthetic construct: amino acid sequence(X')

<400> SEQUENCE: 10

Gly Arg Gly Arg Pro
1               5

<210> SEQ ID NO 11
<211> LENGTH: 5
<212> TYPE: PRT
<213> ORGANISM: artificial sequence
<220> FEATURE:
<223> OTHER INFORMATION: Synthetic construct: amino acid sequence(Z)

<400> SEQUENCE: 11

Val Ala Ala Gly Tyr
1               5

<210> SEQ ID NO 12
<211> LENGTH: 5
<212> TYPE: PRT
<213> ORGANISM: artificial sequence
<220> FEATURE:
<223> OTHER INFORMATION: Synthetic construct: amino acid sequence(Z)

<400> SEQUENCE: 12

Gly Ala Ala Gly Tyr
1               5

<210> SEQ ID NO 13
<211> LENGTH: 33
<212> TYPE: PRT
<213> ORGANISM: Artificial Sequence
<220> FEATURE:
<223> OTHER INFORMATION: Synthetic construct: amino acid sequence(T)

<400> SEQUENCE: 13

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met

<210> SEQ ID NO 14
<211> LENGTH: 12
<212> TYPE: PRT
<213> ORGANISM: Artificial Sequence
<220> FEATURE:
<223> OTHER INFORMATION: Synthetic construct: polypeptide chain(S)

<400> SEQUENCE: 14

Gly Ala Gly Ala Gly Ser Gly Ala Gly Ala Gly Ser
1               5                   10
```

<210> SEQ ID NO 15
<211> LENGTH: 950
<212> TYPE: PRT
<213> ORGANISM: Artificial Sequence
<220> FEATURE:
<223> OTHER INFORMATION: Synthetic construct: protein SELP0K

<400> SEQUENCE: 15

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Lys Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
    130                 135                 140

Ala Gly Ala Gly Ser Gly Val Gly Val Pro Gly Val Gly Val Pro Gly
145                 150                 155                 160

Val Gly Val Pro Gly Val Gly Val Pro Gly Lys Gly Val Pro Gly Val
                165                 170                 175

Gly Val Pro Gly Val Gly Val Pro Gly Val Gly Val Pro Gly Ala Gly
            180                 185                 190

Ala Gly Ser Gly Ala Gly Ala Gly Ser Gly Val Gly Val Pro Gly Val
        195                 200                 205

Gly Val Pro Gly Val Gly Val Pro Gly Val Gly Val Pro Gly Lys Gly
    210                 215                 220

Val Pro Gly Val Gly Val Pro Gly Val Gly Val Pro Gly Val Gly Val
225                 230                 235                 240

Pro Gly Ala Gly Ala Gly Ser Gly Ala Gly Ala Gly Ser Gly Val Gly
                245                 250                 255

Val Pro Gly Val Gly Val Pro Gly Val Gly Val Pro Gly Val Gly Val
            260                 265                 270

Pro Gly Lys Gly Val Pro Gly Val Gly Val Pro Gly Val Gly Val Pro
        275                 280                 285

Gly Val Gly Val Pro Gly Ala Gly Ala Gly Ser Gly Ala Gly Ala Gly
    290                 295                 300

Ser Gly Val Gly Val Pro Gly Val Gly Val Pro Gly Val Gly Val Pro
305                 310                 315                 320

Gly Val Gly Val Pro Gly Lys Gly Val Pro Gly Val Gly Val Pro Gly
                325                 330                 335

Val Gly Val Pro Gly Val Gly Val Pro Gly Ala Gly Ala Gly Ser Gly
            340                 345                 350

Ala Gly Ala Gly Ser Gly Val Gly Val Pro Gly Val Gly Val Pro Gly
        355                 360                 365
```

```
Val Gly Val Pro Gly Val Gly Val Pro Gly Lys Gly Val Pro Gly Val
            370                 375                 380

Gly Val Pro Gly Val Gly Val Pro Gly Val Gly Val Pro Gly Ala Gly
385                 390                 395                 400

Ala Gly Ser Gly Ala Gly Ala Gly Ser Gly Val Gly Val Pro Gly Val
                405                 410                 415

Gly Val Pro Gly Val Gly Val Pro Gly Val Gly Val Pro Gly Lys Gly
            420                 425                 430

Val Pro Gly Val Gly Val Pro Gly Val Gly Val Pro Gly Val Gly Val
        435                 440                 445

Pro Gly Ala Gly Ala Gly Ser Gly Ala Gly Ala Gly Ser Gly Val Gly
    450                 455                 460

Val Pro Gly Val Gly Val Pro Gly Val Gly Val Pro Gly Val Gly Val
465                 470                 475                 480

Pro Gly Lys Gly Val Pro Gly Val Gly Val Pro Gly Val Gly Val Pro
            485                 490                 495

Gly Val Gly Val Pro Gly Ala Gly Ala Gly Ser Gly Ala Gly Ala Gly
            500                 505                 510

Ser Gly Val Gly Val Pro Gly Val Gly Val Pro Gly Val Gly Val Pro
            515                 520                 525

Gly Val Gly Val Pro Gly Lys Gly Val Pro Gly Val Gly Val Pro Gly
            530                 535                 540

Val Gly Val Pro Gly Val Gly Val Pro Gly Ala Gly Ala Gly Ser Gly
545                 550                 555                 560

Ala Gly Ala Gly Ser Gly Val Gly Val Pro Gly Val Gly Val Pro Gly
                565                 570                 575

Val Gly Val Pro Gly Val Gly Val Pro Gly Lys Gly Val Pro Gly Val
            580                 585                 590

Gly Val Pro Gly Val Gly Val Pro Gly Val Gly Val Pro Gly Ala Gly
            595                 600                 605

Ala Gly Ser Gly Ala Gly Ala Gly Ser Gly Val Gly Val Pro Gly Val
    610                 615                 620

Gly Val Pro Gly Val Gly Val Pro Gly Val Gly Val Pro Gly Lys Gly
625                 630                 635                 640

Val Pro Gly Val Gly Val Pro Gly Val Gly Val Pro Gly Val Gly Val
            645                 650                 655

Pro Gly Ala Gly Ala Gly Ser Gly Ala Gly Ala Gly Ser Gly Val Gly
            660                 665                 670

Val Pro Gly Val Gly Val Pro Gly Val Gly Val Pro Gly Val Gly Val
            675                 680                 685

Pro Gly Lys Gly Val Pro Gly Val Gly Val Pro Gly Val Gly Val Pro
    690                 695                 700

Gly Val Gly Val Pro Gly Ala Gly Ala Gly Ser Gly Ala Gly Ala Gly
705                 710                 715                 720

Ser Gly Val Gly Val Pro Gly Val Gly Val Pro Gly Val Gly Val Pro
                725                 730                 735

Gly Val Gly Val Pro Gly Lys Gly Val Pro Gly Val Gly Val Pro Gly
            740                 745                 750

Val Gly Val Pro Gly Val Gly Val Pro Gly Ala Gly Ala Gly Ser Gly
            755                 760                 765

Ala Gly Ala Gly Ser Gly Val Gly Val Pro Gly Val Gly Val Pro Gly
    770                 775                 780

Val Gly Val Pro Gly Val Gly Val Pro Gly Lys Gly Val Pro Gly Val
```

```
                    785                 790                 795                 800

Gly Val Pro Gly Val Gly Val Pro Gly Val Gly Val Pro Gly Ala Gly
                805                 810                 815

Ala Gly Ser Gly Ala Gly Ala Gly Ser Gly Val Gly Val Pro Gly Val
            820                 825                 830

Gly Val Pro Gly Val Gly Val Pro Gly Val Gly Val Pro Gly Lys Gly
        835                 840                 845

Val Pro Gly Val Gly Val Pro Gly Val Gly Val Pro Gly Val Gly Val
    850                 855                 860

Pro Gly Ala Gly Ala Gly Ser Gly Ala Gly Ala Gly Ser Gly Val Gly
865                 870                 875                 880

Val Pro Gly Val Gly Val Pro Gly Val Gly Val Pro Gly Val Gly Val
                885                 890                 895

Pro Gly Lys Gly Val Pro Gly Val Gly Val Pro Gly Val Gly Val Pro
            900                 905                 910

Gly Val Gly Val Pro Gly Ala Gly Ala Gly Ser Gly Ala Gly Ala Gly
        915                 920                 925

Ser Gly Ala Gly Ala Met Asp Pro Gly Arg Tyr Gln Asp Leu Arg Ser
    930                 935                 940

His His His His His His
945                 950

<210> SEQ ID NO 16
<211> LENGTH: 48
<212> TYPE: PRT
<213> ORGANISM: Artificial Sequence
<220> FEATURE:
<223> OTHER INFORMATION: Synthetic construct: polypeptide chain(S)

<400> SEQUENCE: 16

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

<210> SEQ ID NO 17
<211> LENGTH: 40
<212> TYPE: PRT
<213> ORGANISM: Artificial Sequence
<220> FEATURE:
<223> OTHER INFORMATION: Synthetic construct: polypeptide chain(Y)

<400> SEQUENCE: 17

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro
        35                  40

<210> SEQ ID NO 18
<211> LENGTH: 308
<212> TYPE: PRT
<213> ORGANISM: Artificial Sequence
<220> FEATURE:
<223> OTHER INFORMATION: Synthetic construct: protein(A)

<400> SEQUENCE: 18
```

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65              70                  75                  80

Ala Gly Ala Gly Ser Gly Ala Gly Ser Gly Ala Gly Ala Gly Ala Gly
            85                  90                  95

Ser Gly Val Gly Val Pro Gly Val Gly Val Pro Gly Val Gly Val Pro
        100                 105                 110

Gly Val Gly Val Pro Gly Lys Gly Val Pro Gly Val Gly Val Pro Gly
            115                 120                 125

Val Gly Val Pro Gly Val Gly Val Pro Gly Ala Gly Ala Gly Ser Gly
    130                 135                 140

Ala Gly Ala Gly Ser Gly Ala Gly Ala Gly Ser Gly Ala Gly Ala Gly
145                 150                 155                 160

Ser Gly Val Gly Val Pro Gly Val Gly Val Pro Gly Val Gly Val Pro
            165                 170                 175

Gly Val Gly Val Pro Gly Lys Gly Val Pro Gly Val Gly Val Pro Gly
            180                 185                 190

Val Gly Val Pro Gly Val Gly Val Pro Gly Ala Gly Ala Gly Ser Gly
        195                 200                 205

Ala Gly Ala Gly Ser Gly Ala Gly Ala Gly Ser Gly Ala Gly Ala Gly
    210                 215                 220

Ser Gly Val Gly Val Pro Gly Val Gly Val Pro Gly Val Gly Val Pro
225                 230                 235                 240

Gly Val Gly Val Pro Gly Lys Gly Val Pro Gly Val Gly Val Pro Gly
            245                 250                 255

Val Gly Val Pro Gly Val Gly Val Pro Gly Ala Gly Ala Gly Ser Gly
        260                 265                 270

Ala Gly Ala Gly Ser Gly Ala Gly Ser Gly Ala Gly Ala Gly Ala Gly
            275                 280                 285

Ser Gly Ala Met Asp Pro Gly Arg Tyr Gln Asp Leu Arg Ser His His
        290                 295                 300

His His His His
305

<210> SEQ ID NO 19
<211> LENGTH: 1972
<212> TYPE: PRT
<213> ORGANISM: Artificial Sequence
<220> FEATURE:
<223> OTHER INFORMATION: Synthetic construct: polypeptide chain(Y)

<400> SEQUENCE: 19

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
            50                  55                  60

Val Gly Val Pro Gly Val Gly Val Pro Gly Ala Gly Ala Gly Ser Gly
 65                  70                  75                  80

Ala Gly Ala Gly Ser Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
            115                 120                 125

Val Gly Val Pro Gly Val Gly Val Pro Gly Ala Gly Ala Gly Ser Gly
130                 135                 140

Ala Gly Ala Gly Ser Gly Ala Gly Ala Gly Ser Gly Ala Gly Ala Gly
145                 150                 155                 160

Ser Gly Val Gly Val Pro Gly Val Gly Val Pro Gly Val Gly Val Pro
            165                 170                 175

Gly Val Gly Val Pro Gly Lys Gly Val Pro Gly Val Gly Val Pro Gly
            180                 185                 190

Val Gly Val Pro Gly Val Gly Val Pro Gly Ala Gly Ala Gly Ser Gly
            195                 200                 205

Ala Gly Ala Gly Ser Gly Ala Gly Ala Gly Ser Gly Ala Gly Ala Gly
    210                 215                 220

Ser Gly Val Gly Val Pro Gly Val Gly Val Pro Gly Val Gly Val Pro
225                 230                 235                 240

Gly Val Gly Val Pro Gly Lys Gly Val Pro Gly Val Gly Val Pro Gly
            245                 250                 255

Val Gly Val Pro Gly Val Gly Val Pro Gly Ala Gly Ala Gly Ser Gly
            260                 265                 270

Ala Gly Ala Gly Ser Gly Ala Gly Ala Gly Ser Gly Ala Gly Ala Gly
        275                 280                 285

Ser Gly Val Gly Val Pro Gly Val Gly Val Pro Gly Val Gly Val Pro
    290                 295                 300

Gly Val Gly Val Pro Gly Lys Gly Val Pro Gly Val Gly Val Pro Gly
305                 310                 315                 320

Val Gly Val Pro Gly Val Gly Val Pro Gly Ala Gly Ala Gly Ser Gly
            325                 330                 335

Ala Gly Ala Gly Ser Gly Ala Gly Ala Gly Ser Gly Ala Gly Ala Gly
            340                 345                 350

Ser Gly Val Gly Val Pro Gly Val Gly Val Pro Gly Val Gly Val Pro
    355                 360                 365

Gly Val Gly Val Pro Gly Lys Gly Val Pro Gly Val Gly Val Pro Gly
    370                 375                 380

Val Gly Val Pro Gly Val Gly Val Pro Gly Ala Gly Ala Gly Ser Gly
385                 390                 395                 400

Ala Gly Ala Gly Ser Gly Ala Gly Ala Gly Ser Gly Ala Gly Ala Gly
            405                 410                 415

Ser Gly Val Gly Val Pro Gly Val Gly Val Pro Gly Val Gly Val Pro
            420                 425                 430

Gly Val Gly Val Pro Gly Lys Gly Val Pro Gly Val Gly Val Pro Gly
        435                 440                 445

Val Gly Val Pro Gly Val Gly Val Pro Gly Ala Gly Ala Gly Ser Gly
    450                 455                 460

-continued

```
Ala Gly Ala Gly Ser Gly Ala Gly Ala Gly Ser Gly Ala Gly Ala Gly
465                 470                 475                 480

Ser Gly Val Gly Val Pro Gly Val Gly Val Pro Gly Val Gly Val Pro
                485                 490                 495

Gly Val Gly Val Pro Gly Lys Gly Val Pro Gly Val Gly Val Pro Gly
            500                 505                 510

Val Gly Val Pro Gly Val Gly Val Pro Gly Ala Gly Ala Gly Ser Gly
        515                 520                 525

Ala Gly Ala Gly Ser Gly Ala Gly Ala Gly Ser Gly Ala Gly Ala Gly
    530                 535                 540

Ser Gly Val Gly Val Pro Gly Val Gly Val Pro Gly Val Gly Val Pro
545                 550                 555                 560

Gly Val Gly Val Pro Gly Lys Gly Val Pro Gly Val Gly Val Pro Gly
                565                 570                 575

Val Gly Val Pro Gly Val Gly Val Pro Gly Ala Gly Ala Gly Ser Gly
            580                 585                 590

Ala Gly Ala Gly Ser Gly Ala Gly Ala Gly Ser Gly Ala Gly Ala Gly
        595                 600                 605

Ser Gly Val Gly Val Pro Gly Val Gly Val Pro Gly Val Gly Val Pro
    610                 615                 620

Gly Val Gly Val Pro Gly Lys Gly Val Pro Gly Val Gly Val Pro Gly
625                 630                 635                 640

Val Gly Val Pro Gly Val Gly Val Pro Gly Ala Gly Ala Gly Ser Gly
                645                 650                 655

Ala Gly Ala Gly Ser Gly Ala Gly Ala Gly Ser Gly Ala Gly Ala Gly
            660                 665                 670

Ser Gly Val Gly Val Pro Gly Val Gly Val Pro Gly Val Gly Val Pro
        675                 680                 685

Gly Val Gly Val Pro Gly Lys Gly Val Pro Gly Val Gly Val Pro Gly
    690                 695                 700

Val Gly Val Pro Gly Val Gly Val Pro Gly Ala Gly Ala Gly Ser Gly
705                 710                 715                 720

Ala Gly Ala Gly Ser Gly Ala Gly Ala Gly Ser Gly Ala Gly Ala Gly
                725                 730                 735

Ser Gly Val Gly Val Pro Gly Val Gly Val Pro Gly Val Gly Val Pro
            740                 745                 750

Gly Val Gly Val Pro Gly Lys Gly Val Pro Gly Val Gly Val Pro Gly
        755                 760                 765

Val Gly Val Pro Gly Val Gly Val Pro Gly Ala Gly Ala Gly Ser Gly
    770                 775                 780

Ala Gly Ala Gly Ser Gly Ala Gly Ala Gly Ser Gly Ala Gly Ala Gly
785                 790                 795                 800

Ser Gly Val Gly Val Pro Gly Val Gly Val Pro Gly Val Gly Val Pro
                805                 810                 815

Gly Val Gly Val Pro Gly Lys Gly Val Pro Gly Val Gly Val Pro Gly
            820                 825                 830

Val Gly Val Pro Gly Val Gly Val Pro Gly Ala Gly Ala Gly Ser Gly
        835                 840                 845

Ala Gly Ala Gly Ser Gly Ala Gly Ala Gly Ser Gly Ala Gly Ala Gly
    850                 855                 860

Ser Gly Val Gly Val Pro Gly Val Gly Val Pro Gly Val Gly Val Pro
865                 870                 875                 880

Gly Val Gly Val Pro Gly Lys Gly Val Pro Gly Val Gly Val Pro Gly
```

```
                          885                 890                 895
    Val Gly Val Pro Gly Val Gly Val Pro Gly Ala Gly Ala Gly Ser Gly
                    900                 905                 910
    Ala Gly Ala Gly Ser Gly Ala Gly Ala Gly Ser Gly Ala Gly Ala Gly
                915                 920                 925
    Ser Gly Val Gly Val Pro Gly Val Gly Val Pro Gly Val Gly Val Pro
         930                 935                 940
    Gly Val Gly Val Pro Gly Lys Gly Val Pro Gly Val Gly Val Pro Gly
    945                 950                 955                 960
    Val Gly Val Pro Gly Val Gly Val Pro Gly Ala Gly Ala Gly Ser Gly
                    965                 970                 975
    Ala Gly Ala Gly Ser Gly Ala Gly Ala Gly Ser Gly Ala Gly Ala Gly
                980                 985                 990
    Ser Gly Val Gly Val Pro Gly Val Gly Val Pro Gly Val Gly Val Pro
         995                 1000                1005
    Gly Val Gly Val Pro Gly Lys Gly Val Pro Gly Val Gly Val Pro
         1010                1015                1020
    Gly Val Gly Val Pro Gly Val Gly Val Pro Gly Ala Gly Ala Gly
         1025                1030                1035
    Ser Gly Ala Gly Ala Gly Ser Gly Ala Gly Ala Gly Ser Gly Ala
         1040                1045                1050
    Gly Ala Gly Ser Gly Val Gly Val Pro Gly Val Gly Val Pro Gly
         1055                1060                1065
    Val Gly Val Pro Gly Val Gly Val Pro Gly Lys Gly Val Pro Gly
         1070                1075                1080
    Val Gly Val Pro Gly Val Gly Val Pro Gly Val Gly Val Pro Gly
         1085                1090                1095
    Ala Gly Ala Gly Ser Gly Ala Gly Ala Gly Ser Gly Ala Gly Ala
         1100                1105                1110
    Gly Ser Gly Ala Gly Ala Gly Ser Gly Val Gly Val Pro Gly Val
         1115                1120                1125
    Gly Val Pro Gly Val Gly Val Pro Gly Val Gly Val Pro Gly Lys
         1130                1135                1140
    Gly Val Pro Gly Val Gly Val Pro Gly Val Gly Val Pro Gly Val
         1145                1150                1155
    Gly Val Pro Gly Ala Gly Ala Gly Ser Gly Ala Gly Ala Gly Ser
         1160                1165                1170
    Gly Ala Gly Ala Gly Ser Gly Ala Gly Ala Gly Ser Gly Val Gly
         1175                1180                1185
    Val Pro Gly Val Gly Val Pro Gly Val Gly Val Pro Gly Val Gly
         1190                1195                1200
    Val Pro Gly Lys Gly Val Pro Gly Val Gly Val Pro Gly Val Gly
         1205                1210                1215
    Val Pro Gly Val Gly Val Pro Gly Ala Gly Ala Gly Ser Gly Ala
         1220                1225                1230
    Gly Ala Gly Ser Gly Ala Gly Ala Gly Ser Gly Ala Gly Ala Gly
         1235                1240                1245
    Ser Gly Val Gly Val Pro Gly Val Gly Val Pro Gly Val Gly Val
         1250                1255                1260
    Pro Gly Val Gly Val Pro Gly Lys Gly Val Pro Gly Val Gly Val
         1265                1270                1275
    Pro Gly Val Gly Val Pro Gly Val Gly Val Pro Gly Ala Gly Ala
         1280                1285                1290
```

```
Gly Ser Gly Ala Gly Ala Gly Ser Gly Ala Gly Ser Gly
    1295                1300                1305

Ala Gly Ala Gly Ser Gly Val Gly Val Pro Gly Val Pro
    1310                1315                1320

Gly Val Gly Val Pro Gly Val Gly Val Pro Gly Lys Gly Val Pro
    1325                1330                1335

Gly Val Gly Val Pro Gly Val Gly Val Pro Gly Val Gly Val Pro
    1340                1345                1350

Gly Ala Gly Ala Gly Ser Gly Ala Gly Ala Gly Ser Gly Ala Gly
    1355                1360                1365

Ala Gly Ser Gly Ala Gly Ala Gly Ser Gly Val Gly Val Pro Gly
    1370                1375                1380

Val Gly Val Pro Gly Val Gly Val Pro Gly Val Gly Val Pro Gly
    1385                1390                1395

Lys Gly Val Pro Gly Val Gly Val Pro Gly Val Gly Val Pro Gly
    1400                1405                1410

Val Gly Val Pro Gly Ala Gly Ala Gly Ser Gly Ala Gly Ala Gly
    1415                1420                1425

Ser Gly Ala Gly Ala Gly Ser Gly Ala Gly Ala Gly Ser Gly Val
    1430                1435                1440

Gly Val Pro Gly Val Gly Val Pro Gly Val Gly Val Pro Gly Val
    1445                1450                1455

Gly Val Pro Gly Lys Gly Val Pro Gly Val Gly Val Pro Gly Val
    1460                1465                1470

Gly Val Pro Gly Val Gly Val Pro Gly Ala Gly Ala Gly Ser Gly
    1475                1480                1485

Ala Gly Ala Gly Ser Gly Ala Gly Ala Gly Ser Gly Ala Gly Ala
    1490                1495                1500

Gly Ser Gly Val Gly Val Pro Gly Val Gly Val Pro Gly Val Gly
    1505                1510                1515

Val Pro Gly Val Gly Val Pro Gly Lys Gly Val Pro Gly Val Gly
    1520                1525                1530

Val Pro Gly Val Gly Val Pro Gly Val Gly Val Pro Gly Ala Gly
    1535                1540                1545

Ala Gly Ser Gly Ala Gly Ala Gly Ser Gly Ala Gly Ala Gly Ser
    1550                1555                1560

Gly Ala Gly Ala Gly Ser Gly Val Gly Val Pro Gly Val Gly Val
    1565                1570                1575

Pro Gly Val Gly Val Pro Gly Val Gly Val Pro Gly Lys Gly Val
    1580                1585                1590

Pro Gly Val Gly Val Pro Gly Val Gly Val Pro Gly Val Gly Val
    1595                1600                1605

Pro Gly Ala Gly Ala Gly Ser Gly Ala Gly Ala Gly Ser Gly Ala
    1610                1615                1620

Gly Ala Gly Ser Gly Ala Gly Ala Gly Ser Gly Val Gly Val Pro
    1625                1630                1635

Gly Val Gly Val Pro Gly Val Gly Val Pro Gly Val Gly Val Pro
    1640                1645                1650

Gly Lys Gly Val Pro Gly Val Gly Val Pro Gly Val Gly Val Pro
    1655                1660                1665

Gly Val Gly Val Pro Gly Ala Gly Ala Gly Ser Gly Ala Gly Ala
    1670                1675                1680
```

```
Gly Ser Gly Ala Gly Ala Gly Ser Gly Ala Gly Ala Gly Ser Gly
    1685                1690                1695
Val Gly Val Pro Gly Val Gly Val Pro Gly Val Gly Val Pro Gly
    1700                1705                1710
Val Gly Val Pro Gly Lys Gly Val Pro Gly Val Gly Val Pro Gly
    1715                1720                1725
Val Gly Val Pro Gly Val Gly Val Pro Gly Ala Gly Ala Gly Ser
    1730                1735                1740
Gly Ala Gly Ala Gly Ser Gly Ala Gly Ala Gly Ser Gly Ala Gly
    1745                1750                1755
Ala Gly Ser Gly Val Gly Val Pro Gly Val Gly Val Pro Gly Val
    1760                1765                1770
Gly Val Pro Gly Val Gly Val Pro Gly Lys Gly Val Pro Gly Val
    1775                1780                1785
Gly Val Pro Gly Val Gly Val Pro Gly Val Gly Val Pro Gly Ala
    1790                1795                1800
Gly Ala Gly Ser Gly Ala Gly Ala Gly Ser Gly Ala Gly Ala Gly
    1805                1810                1815
Ser Gly Ala Gly Ala Gly Ser Gly Val Gly Val Pro Gly Val Gly
    1820                1825                1830
Val Pro Gly Val Gly Val Pro Gly Val Gly Val Pro Gly Lys Gly
    1835                1840                1845
Val Pro Gly Val Gly Val Pro Gly Val Gly Val Pro Gly Val Gly
    1850                1855                1860
Val Pro Gly Ala Gly Ala Gly Ser Gly Ala Gly Ala Gly Ser Gly
    1865                1870                1875
Ala Gly Ala Gly Ser Gly Ala Gly Ala Gly Ser Gly Val Gly Val
    1880                1885                1890
Pro Gly Val Gly Val Pro Gly Val Gly Val Pro Gly Val Gly Val
    1895                1900                1905
Pro Gly Lys Gly Val Pro Gly Val Gly Val Pro Gly Val Gly Val
    1910                1915                1920
Pro Gly Val Gly Val Pro Gly Ala Gly Ala Gly Ser Gly Ala Gly
    1925                1930                1935
Ala Gly Ser Gly Ala Gly Ala Gly Ser Gly Ala Gly Ala Gly Ser
    1940                1945                1950
Gly Ala Met Asp Pro Gly Arg Tyr Gln Asp Leu Arg Ser His His
    1955                1960                1965
His His His His
    1970

<210> SEQ ID NO 20
<211> LENGTH: 180
<212> TYPE: PRT
<213> ORGANISM: Artificial Sequence
<220> FEATURE:
<223> OTHER INFORMATION: Synthetic construct: protein(A)

<400> SEQUENCE: 20

Met Asp Pro Val Val Leu Gln Arg Arg Asp Trp Glu Asn Pro Gly
1               5                   10                  15
Thr Gln Leu Asn Arg Leu Ala Ala His Pro Pro Phe Ala Ser Asp Pro
                20                  25                  30
Met Gly Val Gly Val Pro Gly Val Gly Val Pro Gly Val Gly Val Pro
                35                  40                  45
```

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
    130                 135                 140

Ala Gly Ala Gly Ser Gly Ala Gly Ala Gly Ser Gly Ala Gly Ala Gly
145                 150                 155                 160

Ser Gly Ala Met Asp Pro Gly Arg Tyr Gln Asp Leu Arg Ser His His
                165                 170                 175

His His His His
        180

<210> SEQ ID NO 21
<211> LENGTH: 60
<212> TYPE: PRT
<213> ORGANISM: Artificial Sequence
<220> FEATURE:
<223> OTHER INFORMATION: Synthetic construct: polypeptide chain(Y')

<400> SEQUENCE: 21

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Lys
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro
    50                  55                  60

<210> SEQ ID NO 22
<211> LENGTH: 36
<212> TYPE: PRT
<213> ORGANISM: Artificial Sequence
<220> FEATURE:
<223> OTHER INFORMATION: Synthetic construct: polypeptide chain(S)

<400> SEQUENCE: 22

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser
        35

<210> SEQ ID NO 23
<211> LENGTH: 200
<212> TYPE: PRT
<213> ORGANISM: Artificial Sequence
<220> FEATURE:
<223> OTHER INFORMATION: Synthetic construct: polypeptide chain(Y)

<400> SEQUENCE: 23

Gly Val Gly Val Pro Gly Val Gly Val Pro Gly Val Gly Val Pro Gly

```
              1               5                   10                  15
Val Gly Val Pro Gly Val Gly Val Pro Gly Val Gly Val Pro Gly Val
                    20                  25                  30
Gly Val Pro Gly Val Gly Val Pro Gly Val Gly Val Pro Gly Val Gly
                    35                  40                  45
Val Pro Gly Val Gly Val Pro Gly Val Gly Val Pro Gly Val Gly Val
                    50                  55                  60
Pro Gly Val Gly Val Pro Gly Val Gly Val Pro Gly Val Gly Val Pro
 65                 70                  75                  80
Gly Val Gly Val Pro Gly Val Gly Val Pro Gly Val Gly Val Pro Gly
                    85                  90                  95
Val Gly Val Pro Gly Val Gly Val Pro Gly Val Gly Val Pro Gly Val
                    100                 105                 110
Gly Val Pro Gly Val Gly Val Pro Gly Val Gly Val Pro Gly Val Gly
                    115                 120                 125
Val Pro Gly Val Gly Val Pro Gly Val Gly Val Pro Gly Val Gly Val
                    130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                    165                 170                 175
Val Gly Val Pro Gly Val Gly Val Pro Gly Val Gly Val Pro Gly Val
                    180                 185                 190
Gly Val Pro Gly Val Gly Val Pro
                    195                 200

<210> SEQ ID NO 24
<211> LENGTH: 1192
<212> TYPE: PRT
<213> ORGANISM: Artificial Sequence
<220> FEATURE:
<223> OTHER INFORMATION: Synthetic construct: protein(A)

<400> SEQUENCE: 24

Met Asp Pro Val Val Leu Gln Arg Arg Asp Trp Glu Asn Pro Gly Val
 1               5                   10                  15
Thr Gln Leu Asn Arg Leu Ala Ala His Pro Pro Phe Ala Ser Asp Pro
                20                  25                  30
Met Gly Val Gly Val Pro Gly Val Gly Val Pro Gly Val Gly Val Pro
                35                  40                  45
Gly Val Gly Val Pro Gly Lys Gly Val Pro Gly Val Gly Val Pro Gly
             50                  55                  60
Val Gly Val Pro Gly Val Gly Val Pro Gly Ala Gly Ala Gly Ser Gly
 65                 70                  75                  80
Ala Gly Ala Gly Ser Gly Ala Gly Ala Gly Ser Gly Ala Gly Ala Gly
                    85                  90                  95
Ser Gly Ala Gly Ala Gly Ser Gly Ala Gly Ala Gly Ser Gly Val Gly
                    100                 105                 110
Val Pro Gly Val Gly Val Pro Gly Val Gly Val Pro Gly Val Gly Val
                    115                 120                 125
Pro Gly Lys Gly Val Pro Gly Val Gly Val Pro Gly Val Gly Val Pro
                130                 135                 140
Gly Val Gly Val Pro Gly Ala Gly Ala Gly Ser Gly Ala Gly Ala Gly
145                 150                 155                 160
Ser Gly Ala Gly Ala Gly Ser Gly Ala Gly Ala Gly Ser Gly Ala Gly
```

```
            165                 170                 175
Ala Gly Ser Gly Ala Gly Ala Gly Ser Gly Val Gly Val Pro Gly Val
            180                 185                 190
Gly Val Pro Gly Val Gly Val Pro Gly Val Gly Val Pro Gly Lys Gly
            195                 200                 205
Val Pro Gly Val Gly Val Pro Gly Val Gly Val Pro Gly Val Gly Val
            210                 215                 220
Pro Gly Ala Gly Ala Gly Ser Gly Ala Gly Ala Gly Ser Gly Ala Gly
225                 230                 235                 240
Ala Gly Ser Gly Ala Gly Ala Gly Ser Gly Ala Gly Ala Gly Ser Gly
            245                 250                 255
Ala Gly Ala Gly Ser Gly Val Gly Val Pro Gly Val Gly Val Pro Gly
            260                 265                 270
Val Gly Val Pro Gly Val Gly Val Pro Gly Lys Gly Val Pro Gly Val
            275                 280                 285
Gly Val Pro Gly Val Gly Val Pro Gly Val Gly Val Pro Gly Ala Gly
            290                 295                 300
Ala Gly Ser Gly Ala Gly Ala Gly Ser Gly Ala Gly Ala Gly Ser Gly
305                 310                 315                 320
Ala Gly Ala Gly Ser Gly Ala Gly Ala Gly Ser Gly Ala Gly Ala Gly
            325                 330                 335
Ser Gly Val Gly Val Pro Gly Val Gly Val Pro Gly Val Gly Val Pro
            340                 345                 350
Gly Val Gly Val Pro Gly Lys Gly Val Pro Gly Val Gly Val Pro Gly
            355                 360                 365
Val Gly Val Pro Gly Val Gly Val Pro Gly Ala Gly Ala Gly Ser Gly
            370                 375                 380
Ala Gly Ala Gly Ser Gly Ala Gly Ala Gly Ser Gly Ala Gly Ala Gly
385                 390                 395                 400
Ser Gly Ala Gly Ala Gly Ser Gly Ala Gly Ala Gly Ser Gly Val Gly
            405                 410                 415
Val Pro Gly Val Gly Val Pro Gly Val Gly Val Pro Gly Val Gly Val
            420                 425                 430
Pro Gly Lys Gly Val Pro Gly Val Gly Val Pro Gly Val Gly Val Pro
            435                 440                 445
Gly Val Gly Val Pro Gly Ala Gly Ala Gly Ser Gly Ala Gly Ala Gly
            450                 455                 460
Ser Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
            485                 490                 495
Gly Val Pro Gly Val Gly Val Pro Gly Val Gly Val Pro Gly Lys Gly
            500                 505                 510
Val Pro Gly Val Gly Val Pro Gly Val Gly Val Pro Gly Val Gly Val
            515                 520                 525
Pro Gly Ala Gly Ala Gly Ser Gly Ala Gly Ala Gly Ser Gly Ala Gly
            530                 535                 540
Ala Gly Ser Gly Ala Gly Ala Gly Ser Gly Ala Gly Ala Gly Ser Gly
545                 550                 555                 560
Ala Gly Ala Gly Ser Gly Val Gly Val Pro Gly Val Gly Val Pro Gly
            565                 570                 575
Val Gly Val Pro Gly Val Gly Val Pro Gly Lys Gly Val Pro Gly Val
            580                 585                 590
```

-continued

Gly Val Pro Gly Val Gly Val Pro Gly Val Gly Val Pro Gly Ala Gly
            595                 600                 605

Ala Gly Ser Gly Ala Gly Ala Gly Ser Gly Ala Gly Ala Gly Ser Gly
        610                 615                 620

Ala Gly Ala Gly Ser Gly Ala Gly Ala Gly Ser Gly Ala Gly Ala Gly
625                 630                 635                 640

Ser Gly Val Gly Val Pro Gly Val Gly Val Pro Gly Val Gly Val Pro
            645                 650                 655

Gly Val Gly Val Pro Gly Lys Gly Val Pro Gly Val Gly Val Pro Gly
            660                 665                 670

Val Gly Val Pro Gly Val Gly Val Pro Gly Ala Gly Ala Gly Ser Gly
            675                 680                 685

Ala Gly Ala Gly Ser Gly Ala Gly Ala Gly Ser Gly Ala Gly Ala Gly
        690                 695                 700

Ser Gly Ala Gly Ala Gly Ser Gly Ala Gly Ala Gly Ser Gly Val Gly
705                 710                 715                 720

Val Pro Gly Val Gly Val Pro Gly Val Gly Val Pro Gly Val Gly Val
            725                 730                 735

Pro Gly Lys Gly Val Pro Gly Val Gly Val Pro Gly Val Gly Val Pro
            740                 745                 750

Gly Val Gly Val Pro Gly Ala Gly Ala Gly Ser Gly Ala Gly Ala Gly
            755                 760                 765

Ser Gly Ala Gly Ala Gly Ser Gly Ala Gly Ala Gly Ser Gly Ala Gly
        770                 775                 780

Ala Gly Ser Gly Ala Gly Ala Gly Ser Gly Val Gly Val Pro Gly Val
785                 790                 795                 800

Gly Val Pro Gly Val Gly Val Pro Gly Val Gly Val Pro Gly Lys Gly
            805                 810                 815

Val Pro Gly Val Gly Val Pro Gly Val Gly Val Pro Gly Val Gly Val
            820                 825                 830

Pro Gly Ala Gly Ala Gly Ser Gly Ala Gly Ala Gly Ser Gly Ala Gly
            835                 840                 845

Ala Gly Ser Gly Ala Gly Ala Gly Ser Gly Ala Gly Ala Gly Ser Gly
        850                 855                 860

Ala Gly Ala Gly Ser Gly Val Gly Val Pro Gly Val Gly Val Pro Gly
865                 870                 875                 880

Val Gly Val Pro Gly Val Gly Val Pro Gly Lys Gly Val Pro Gly Val
            885                 890                 895

Gly Val Pro Gly Val Gly Val Pro Gly Val Gly Val Pro Gly Ala Gly
            900                 905                 910

Ala Gly Ser Gly Ala Gly Ala Gly Ser Gly Ala Gly Ala Gly Ser Gly
        915                 920                 925

Ala Gly Ala Gly Ser Gly Ala Gly Ala Gly Ser Gly Ala Gly Ala Gly
        930                 935                 940

Ser Gly Val Gly Val Pro Gly Val Gly Val Pro Gly Val Gly Val Pro
945                 950                 955                 960

Gly Val Gly Val Pro Gly Lys Gly Val Pro Gly Val Gly Val Pro Gly
            965                 970                 975

Val Gly Val Pro Gly Val Gly Val Pro Gly Ala Gly Ala Gly Ser Gly
            980                 985                 990

Ala Gly Ala Gly Ser Gly Ala Gly Ala Gly Ser Gly Ala Gly Ala Gly
        995                 1000                1005

Ser Gly Ala Gly Ala Gly Ser Gly Ala Gly Ala Gly Ser Gly Val
    1010                1015                1020

Gly Val Pro Gly Val Gly Val Pro Gly Val Gly Val Pro Gly Val
    1025                1030                1035

Gly Val Pro Gly Lys Gly Val Pro Gly Val Gly Val Pro Gly Val
    1040                1045                1050

Gly Val Pro Gly Val Gly Val Pro Gly Ala Gly Ala Gly Ser Gly
    1055                1060                1065

Ala Gly Ala Gly Ser Gly Ala Gly Ala Gly Ser Gly Ala Gly Ala
    1070                1075                1080

Gly Ser Gly Ala Gly Ala Gly Ser Gly Ala Gly Ala Gly Ser Gly
    1085                1090                1095

Val Gly Val Pro Gly Val Gly Val Pro Gly Val Gly Val Pro Gly
    1100                1105                1110

Val Gly Val Pro Gly Lys Gly Val Pro Gly Val Gly Val Pro Gly
    1115                1120                1125

Val Gly Val Pro Gly Val Gly Val Pro Gly Ala Gly Ala Gly Ser
    1130                1135                1140

Gly Ala Gly Ala Gly Ser Gly Ala Gly Ala Gly Ser Gly Ala Gly
    1145                1150                1155

Ala Gly Ser Gly Ala Gly Ala Gly Ser Gly Ala Gly Ala Gly Ser
    1160                1165                1170

Gly Ala Met Asp Pro Gly Arg Tyr Gln Asp Leu Arg Ser His His
    1175                1180                1185

His His His His
    1190

<210> SEQ ID NO 25
<211> LENGTH: 1144
<212> TYPE: PRT
<213> ORGANISM: Artificial Sequence
<220> FEATURE:
<223> OTHER INFORMATION: Synthetic construct: protein(A)

<400> SEQUENCE: 25

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Val Gly Val Pro Gly Val Gly Val Pro Gly Ala Gly
                85                  90                  95

Ala Gly Ser Gly Ala Gly Ala Gly Ser Gly Ala Gly Ala Gly Ser Gly
            100                 105                 110

Ala Gly Ala Gly Ser Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Val Pro Gly Lys Gly Val Pro Gly Val Gly Val Pro Gly Val Gly
145                 150                 155                 160

```
Val Pro Gly Val Gly Val Pro Gly Val Gly Val Pro Gly Val
            165                 170                 175

Pro Gly Ala Gly Ala Gly Ser Gly Ala Gly Ala Gly Ser Gly Ala Gly
            180                 185                 190

Ala Gly Ser Gly Ala Gly Ala Gly Ser Gly Val Gly Val Pro Gly Val
            195                 200                 205

Gly Val Pro Gly Val Gly Val Pro Gly Val Gly Val Pro Gly Val Gly
            210                 215                 220

Val Pro Gly Val Gly Val Pro Gly Lys Gly Val Pro Gly Val Gly Val
225                 230                 235                 240

Pro Gly Val Gly Val Pro Gly Val Gly Val Pro Gly Val Gly Val Pro
            245                 250                 255

Gly Val Gly Val Pro Gly Ala Gly Ala Gly Ser Gly Ala Gly Ala Gly
            260                 265                 270

Ser Gly Ala Gly Ala Gly Ser Gly Ala Gly Ala Gly Ser Gly Val Gly
            275                 280                 285

Val Pro Gly Val Gly Val Pro Gly Val Gly Val Pro Gly Val Gly Val
            290                 295                 300

Pro Gly Val Gly Val Pro Gly Val Gly Val Pro Gly Lys Gly Val Pro
305                 310                 315                 320

Gly Val Gly Val Pro Gly Val Gly Val Pro Gly Val Gly Val Pro Gly
            325                 330                 335

Val Gly Val Pro Gly Val Gly Val Pro Gly Ala Gly Ala Gly Ser Gly
            340                 345                 350

Ala Gly Ala Gly Ser Gly Ala Gly Ala Gly Ser Gly Ala Gly Ala Gly
            355                 360                 365

Ser Gly Val Gly Val Pro Gly Val Gly Val Pro Gly Val Gly Val Pro
            370                 375                 380

Gly Val Gly Val Pro Gly Val Gly Val Pro Gly Val Gly Val Pro Gly
385                 390                 395                 400

Lys Gly Val Pro Gly Val Gly Val Pro Gly Val Gly Val Pro Gly Val
            405                 410                 415

Gly Val Pro Gly Val Gly Val Pro Gly Val Gly Val Pro Gly Ala Gly
            420                 425                 430

Ala Gly Ser Gly Ala Gly Ala Gly Ser Gly Ala Gly Ala Gly Ser Gly
            435                 440                 445

Ala Gly Ala Gly Ser Gly Val Gly Val Pro Gly Val Gly Val Pro Gly
            450                 455                 460

Val Gly Val Pro Gly Val Gly Val Pro Gly Val Gly Val Pro Gly Val
465                 470                 475                 480

Gly Val Pro Gly Lys Gly Val Pro Gly Val Gly Val Pro Gly Val Gly
            485                 490                 495

Val Pro Gly Val Gly Val Pro Gly Val Gly Val Pro Gly Val Gly Val
            500                 505                 510

Pro Gly Ala Gly Ala Gly Ser Gly Ala Gly Ala Gly Ser Gly Ala Gly
            515                 520                 525

Ala Gly Ser Gly Ala Gly Ala Gly Ser Gly Val Gly Val Pro Gly Val
            530                 535                 540

Gly Val Pro Gly Val Gly Val Pro Gly Val Gly Val Pro Gly Val Gly
545                 550                 555                 560

Val Pro Gly Val Gly Val Pro Gly Lys Gly Val Pro Gly Val Gly Val
            565                 570                 575

Pro Gly Val Gly Val Pro Gly Val Gly Val Pro Gly Val Gly Val Pro
```

-continued

```
                580                 585                 590
Gly Val Gly Val Pro Gly Ala Gly Ala Gly Ser Gly Ala Gly Ala Gly
            595                 600                 605
Ser Gly Ala Gly Ala Gly Ser Gly Ala Gly Ala Gly Ser Gly Val Gly
            610                 615                 620
Val Pro Gly Val Gly Val Pro Gly Val Gly Val Pro Gly Val Gly Val
625                 630                 635                 640
Pro Gly Val Gly Val Pro Gly Val Gly Val Pro Gly Lys Gly Val Pro
                645                 650                 655
Gly Val Gly Val Pro Gly Val Gly Val Pro Gly Val Gly Val Pro Gly
            660                 665                 670
Val Gly Val Pro Gly Val Gly Val Pro Gly Ala Gly Ala Gly Ser Gly
            675                 680                 685
Ala Gly Ala Gly Ser Gly Ala Gly Ala Gly Ser Gly Ala Gly Ala Gly
            690                 695                 700
Ser Gly Val Gly Val Pro Gly Val Gly Val Pro Gly Val Gly Val Pro
705                 710                 715                 720
Gly Val Gly Val Pro Gly Val Gly Val Pro Gly Val Gly Val Pro Gly
                725                 730                 735
Lys Gly Val Pro Gly Val Gly Val Pro Gly Val Gly Val Pro Gly Val
            740                 745                 750
Gly Val Pro Gly Val Gly Val Pro Gly Val Gly Val Pro Gly Ala Gly
            755                 760                 765
Ala Gly Ser Gly Ala Gly Ala Gly Ser Gly Ala Gly Ala Gly Ser Gly
            770                 775                 780
Ala Gly Ala Gly Ser Gly Val Gly Val Pro Gly Val Gly Val Pro Gly
785                 790                 795                 800
Val Gly Val Pro Gly Val Gly Val Pro Gly Val Gly Val Pro Gly Val
                805                 810                 815
Gly Val Pro Gly Lys Gly Val Pro Gly Val Gly Val Pro Gly Val Gly
            820                 825                 830
Val Pro Gly Val Gly Val Pro Gly Val Gly Val Pro Gly Val Gly Val
            835                 840                 845
Pro Gly Ala Gly Ala Gly Ser Gly Ala Gly Ala Gly Ser Gly Ala Gly
            850                 855                 860
Ala Gly Ser Gly Ala Gly Ala Gly Ser Gly Val Gly Val Pro Gly Val
865                 870                 875                 880
Gly Val Pro Gly Val Gly Val Pro Gly Val Gly Val Pro Gly Val Gly
                885                 890                 895
Val Pro Gly Val Gly Val Pro Gly Lys Gly Val Pro Gly Val Gly Val
            900                 905                 910
Pro Gly Val Gly Val Pro Gly Val Gly Val Pro Gly Val Gly Val Pro
            915                 920                 925
Gly Val Gly Val Pro Gly Ala Gly Ala Gly Ser Gly Ala Gly Ala Gly
            930                 935                 940
Ser Gly Ala Gly Ala Gly Ser Gly Ala Gly Ala Gly Ser Gly Val Gly
945                 950                 955                 960
Val Pro Gly Val Gly Val Pro Gly Val Gly Val Pro Gly Val Gly Val
                965                 970                 975
Pro Gly Val Gly Val Pro Gly Val Gly Val Pro Gly Lys Gly Val Pro
            980                 985                 990
Gly Val Gly Val Pro Gly Val Gly  Val Pro Gly Val Gly  Val Pro Gly
            995                 1000                1005
```

-continued

Val Gly Val Pro Gly Val Gly Val Pro Gly Ala Gly Ala Gly Ser
    1010            1015                1020

Gly Ala Gly Ala Gly Ser Gly Ala Gly Ala Gly Ser Gly Ala Gly
    1025            1030                1035

Ala Gly Ser Gly Val Gly Val Pro Gly Val Gly Val Pro Gly Val
    1040            1045                1050

Gly Val Pro Gly Val Gly Val Pro Gly Val Gly Val Pro Gly Val
    1055            1060                1065

Gly Val Pro Gly Lys Gly Val Pro Gly Val Gly Val Pro Gly Val
    1070            1075                1080

Gly Val Pro Gly Val Gly Val Pro Gly Val Gly Val Pro Gly Val
    1085            1090                1095

Gly Val Pro Gly Ala Gly Ala Gly Ser Gly Ala Gly Ala Gly Ser
    1100            1105                1110

Gly Ala Gly Ala Gly Ser Gly Ala Gly Ala Gly Ser Gly Ala Met
    1115            1120                1125

Asp Pro Gly Arg Tyr Gln Asp Leu Arg Ser His His His His His
    1130            1135                1140

His

<210> SEQ ID NO 26
<211> LENGTH: 20
<212> TYPE: PRT
<213> ORGANISM: Artificial Sequence
<220> FEATURE:
<223> OTHER INFORMATION: Synthetic construct: polypeptide chain(Y)

<400> SEQUENCE: 26

Val Pro Gly Val Gly Val Pro Gly Val Gly Val Pro Gly Val Gly Val
1               5                   10                  15

Pro Gly Val Gly
            20

<210> SEQ ID NO 27
<211> LENGTH: 884
<212> TYPE: PRT
<213> ORGANISM: Artificial Sequence
<220> FEATURE:
<223> OTHER INFORMATION: Synthetic construct: protein SELP8K

<400> SEQUENCE: 27

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

```
Lys Gly Val Pro Gly Val Gly Val Pro Gly Val Gly Val
130                 135                 140

Gly Val Pro Gly Ala Gly Ala Gly Ser Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
                180                 185                 190

Lys Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
            210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
                245                 250                 255

Lys Gly Val Pro Gly Val Gly Val Pro Gly Val Gly Val Pro Gly Val
            260                 265                 270

Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
            290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
                325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
            370                 375                 380

Lys Gly Val Pro Gly Val Gly Val Pro Gly Val Gly Val Pro Gly Val
385                 390                 395                 400

Gly Val Pro Gly Ala Gly Ala Gly Ser Gly Ala Gly Ala Gly Ser Gly
                405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
            435                 440                 445

Lys Gly Val Pro Gly Val Gly Val Pro Gly Val Gly Val Pro Gly Val
450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
                485                 490                 495

Gly Val Gly Val Pro Gly Val Gly Val Pro Gly Val Gly Val Pro Gly
            500                 505                 510

Lys Gly Val Pro Gly Val Gly Val Pro Gly Val Gly Val Pro Gly Val
            515                 520                 525

Gly Val Pro Gly Ala Gly Ala Gly Ser Gly Ala Gly Ala Gly Ser Gly
            530                 535                 540
```

```
Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
                565                 570                 575

Lys Gly Val Pro Gly Val Gly Val Pro Gly Val Gly Val Pro Gly Val
            580                 585                 590

Gly Val Pro Gly Ala Gly Ala Gly Ser Gly Ala Gly Ala Gly Ser Gly
        595                 600                 605

Ala Gly Ala Gly Ser Gly Ala Gly Ala Gly Ser Gly Val Gly Val Pro
    610                 615                 620

Gly Val Gly Val Pro Gly Val Gly Val Pro Gly Val Gly Val Pro Gly
625                 630                 635                 640

Lys Gly Val Pro Gly Val Gly Val Pro Gly Val Gly Val Pro Gly Val
                645                 650                 655

Gly Val Pro Gly Ala Gly Ala Gly Ser Gly Ala Gly Ala Gly Ser Gly
            660                 665                 670

Ala Gly Ala Gly Ser Gly Ala Gly Ala Gly Ser Gly Val Gly Val Pro
        675                 680                 685

Gly Val Gly Val Pro Gly Val Gly Val Pro Gly Val Gly Val Pro Gly
    690                 695                 700

Lys Gly Val Pro Gly Val Gly Val Pro Gly Val Gly Val Pro Gly Val
705                 710                 715                 720

Gly Val Pro Gly Ala Gly Ala Gly Ser Gly Ala Gly Ala Gly Ser Gly
                725                 730                 735

Ala Gly Ala Gly Ser Gly Ala Gly Ala Gly Ser Gly Val Gly Val Pro
            740                 745                 750

Gly Val Gly Val Pro Gly Val Gly Val Pro Gly Val Gly Val Pro Gly
        755                 760                 765

Lys Gly Val Pro Gly Val Gly Val Pro Gly Val Gly Val Pro Gly Val
    770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
                805                 810                 815

Gly Val Gly Val Pro Gly Val Gly Val Pro Gly Val Gly Val Pro Gly
            820                 825                 830

Lys Gly Val Pro Gly Val Gly Val Pro Gly Val Gly Val Pro Gly Val
        835                 840                 845

Gly Val Pro Gly Ala Gly Ala Gly Ser Gly Ala Gly Ala Gly Ser Gly
    850                 855                 860

Ala Gly Ala Met Asp Pro Gly Arg Tyr Gln Asp Leu Arg Ser His His
865                 870                 875                 880

His His His His

<210> SEQ ID NO 28
<211> LENGTH: 492
<212> TYPE: PRT
<213> ORGANISM: Artificial Sequence
<220> FEATURE:
<223> OTHER INFORMATION: Synthetic construct: protein(A)

<400> SEQUENCE: 28

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
```

```
                    20                  25                  30
Met Val Pro Gly Val Gly Val Pro Gly Val Gly Val Pro Gly Val Gly
                35                  40                  45
Val Pro Gly Val Gly Val Val Pro Gly Val Gly Val Pro Gly Val
 50                  55                  60
Gly Val Pro Gly Val Gly Val Pro Gly Val Gly Val Val Pro Gly
 65                  70                  75                  80
Val Gly Val Pro Gly Val Gly Val Pro Gly Val Gly Val Pro Gly Val
                85                  90                  95
Gly Val Val Val Pro Gly Val Gly Val Pro Gly Val Gly Val Pro Gly
                100                 105                 110
Val Gly Val Pro Gly Val Gly Val Val Pro Gly Val Gly Val Pro
                115                 120                 125
Gly Val Gly Val Pro Gly Val Gly Val Pro Gly Val Gly Val Val Val
                130                 135                 140
Pro Gly Val Gly Val Pro Gly Val Gly Val Pro Gly Val Gly Val Pro
145                 150                 155                 160
Gly Val Gly Val Val Pro Gly Val Gly Val Pro Gly Val Gly Val
                165                 170                 175
Pro Gly Val Gly Val Pro Gly Val Gly Val Val Pro Gly Val Gly
                180                 185                 190
Val Pro Gly Val Gly Val Pro Gly Val Gly Val Pro Gly Val Gly Val
                195                 200                 205
Val Val Pro Gly Val Gly Val Pro Gly Val Gly Val Pro Gly Val Gly
                210                 215                 220
Val Pro Gly Val Gly Val Val Pro Gly Val Gly Val Pro Gly Val
225                 230                 235                 240
Gly Val Pro Gly Val Gly Val Pro Gly Val Gly Val Val Pro Gly
                245                 250                 255
Val Gly Val Pro Gly Val Gly Val Pro Gly Val Gly Val Pro Gly Val
                260                 265                 270
Gly Val Val Val Pro Gly Val Gly Val Pro Gly Val Gly Val Pro Gly
                275                 280                 285
Val Gly Val Pro Gly Val Gly Val Val Pro Gly Val Gly Val Pro
                290                 295                 300
Gly Val Gly Val Pro Gly Val Gly Val Pro Gly Val Gly Val Val Val
305                 310                 315                 320
Pro Gly Val Gly Val Pro Gly Val Gly Val Pro Gly Val Gly Val Pro
                325                 330                 335
Gly Val Gly Val Val Pro Gly Val Gly Val Pro Gly Val Gly Val
                340                 345                 350
Pro Gly Val Gly Val Pro Gly Val Gly Val Val Pro Gly Val Gly
                355                 360                 365
Val Pro Gly Val Gly Val Pro Gly Val Gly Val Pro Gly Val Gly Val
                370                 375                 380
Val Val Pro Gly Val Gly Val Pro Gly Val Gly Val Pro Gly Val Gly
385                 390                 395                 400
Val Pro Gly Val Gly Val Val Pro Gly Val Gly Val Pro Gly Val
                405                 410                 415
Gly Val Pro Gly Val Gly Val Pro Gly Val Gly Val Val Pro Gly
                420                 425                 430
Val Gly Val Pro Gly Val Gly Val Pro Gly Val Gly Val Pro Gly Val
                435                 440                 445
```

```
Gly Val Val Pro Gly Val Gly Val Pro Gly
    450                 455                 460

Val Gly Val Pro Gly Val Gly Val Val Gly Ala Met Asp Pro Gly Arg
465                 470                 475                 480

Tyr Gln Asp Leu Arg Ser His His His His His His
                485                 490

<210> SEQ ID NO 29
<211> LENGTH: 10
<212> TYPE: PRT
<213> ORGANISM: Artificial Sequence
<220> FEATURE:
<223> OTHER INFORMATION: Synthetic construct: polypeptide chain(Y)

<400> SEQUENCE: 29

Gly Val Gly Val Pro Gly Val Gly Val Pro
1               5                   10

<210> SEQ ID NO 30
<211> LENGTH: 1386
<212> TYPE: PRT
<213> ORGANISM: Artificial Sequence
<220> FEATURE:
<223> OTHER INFORMATION: Synthetic construct: protein(A)

<400> SEQUENCE: 30

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ala Gly Ser Gly Ala Gly Ala Gly Ser Gly Ala Gly
            35                  40                  45

Ala Gly Ser Gly Ala Gly Ala Gly Ser Gly Ala Gly Ala Gly Ser Gly
        50                  55                  60

Ala Gly Ala Gly Ser Gly Val Gly Val Pro Gly Val Gly Val Pro Gly
65                  70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Ala Gly Ala Gly Ser Gly Ala Gly
            100                 105                 110

Ala Gly Ser Gly Val Gly Val Pro Gly Val Gly Val Pro Gly Ala Gly
        115                 120                 125

Ala Gly Ser Gly Ala Gly Ala Gly Ser Gly Ala Gly Ala Gly Ser Gly
    130                 135                 140

Ala Gly Ala Gly Ser Gly Ala Gly Ala Gly Ser Gly Ala Gly Ala Gly
145                 150                 155                 160

Ser Gly Val Gly Val Pro Gly Val Gly Val Pro Gly Ala Gly Ala Gly
                165                 170                 175

Ser Gly Ala Gly Ala Gly Ser Gly Ala Gly Ala Gly Ser Gly Ala Gly
            180                 185                 190

Ala Gly Ser Gly Ala Gly Ala Gly Ser Gly Ala Gly Ala Gly Ser Gly
        195                 200                 205

Val Gly Val Pro Gly Val Gly Val Pro Gly Ala Gly Ala Gly Ser Gly
    210                 215                 220

Ala Gly Ala Gly Ser Gly Ala Gly Ala Gly Ser Gly Ala Gly Ala Gly
225                 230                 235                 240

Ser Gly Ala Gly Ala Gly Ser Gly Ala Gly Ala Gly Ser Gly Val Gly
```

```
                        245                 250                 255
Val Pro Gly Val Gly Val Pro Gly Ala Gly Ala Gly Ser Gly Ala Gly
                260                 265                 270

Ala Gly Ser Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
        290                 295                 300

Gly Val Gly Val Pro Gly Ala Gly Ala Gly Ser Gly Ala Gly Ala Gly
305                 310                 315                 320

Ser Gly Ala Gly Ala Gly Ser Gly Ala Gly Ala Gly Ser Gly Ala Gly
                325                 330                 335

Ala Gly Ser Gly Ala Gly Ala Gly Ser Gly Val Gly Val Pro Gly Val
            340                 345                 350

Gly Val Pro Gly Ala Gly Ala Gly Ser Gly Ala Gly Ala Gly Ser Gly
        355                 360                 365

Ala Gly Ala Gly Ser Gly Ala Gly Ala Gly Ser Gly Ala Gly Ala Gly
    370                 375                 380

Ser Gly Ala Gly Ala Gly Ser Gly Val Gly Val Pro Gly Val Gly Val
385                 390                 395                 400

Pro Gly Ala Gly Ala Gly Ser Gly Ala Gly Ala Gly Ser Gly Ala Gly
                405                 410                 415

Ala Gly Ser Gly Ala Gly Ala Gly Ser Gly Ala Gly Ala Gly Ser Gly
            420                 425                 430

Ala Gly Ala Gly Ser Gly Val Gly Val Pro Gly Val Gly Val Pro Gly
        435                 440                 445

Ala Gly Ala Gly Ser Gly Ala Gly Ala Gly Ser Gly Ala Gly Ala Gly
    450                 455                 460

Ser Gly Ala Gly Ala Gly Ser Gly Ala Gly Ala Gly Ser Gly Ala Gly
465                 470                 475                 480

Ala Gly Ser Gly Val Gly Val Pro Gly Val Gly Val Pro Gly Ala Gly
                485                 490                 495

Ala Gly Ser Gly Ala Gly Ala Gly Ser Gly Ala Gly Ala Gly Ser Gly
            500                 505                 510

Ala Gly Ala Gly Ser Gly Ala Gly Ala Gly Ser Gly Ala Gly Ala Gly
        515                 520                 525

Ser Gly Val Gly Val Pro Gly Val Gly Val Pro Gly Ala Gly Ala Gly
    530                 535                 540

Ser Gly Ala Gly Ala Gly Ser Gly Ala Gly Ala Gly Ser Gly Ala Gly
545                 550                 555                 560

Ala Gly Ser Gly Ala Gly Ala Gly Ser Gly Ala Gly Ala Gly Ser Gly
                565                 570                 575

Val Gly Val Pro Gly Val Gly Val Pro Gly Ala Gly Ala Gly Ser Gly
            580                 585                 590

Ala Gly Ala Gly Ser Gly Ala Gly Ala Gly Ser Gly Ala Gly Ala Gly
        595                 600                 605

Ser Gly Ala Gly Ala Gly Ser Gly Ala Gly Ala Gly Ser Gly Val Gly
    610                 615                 620

Val Pro Gly Val Gly Val Pro Gly Ala Gly Ala Gly Ser Gly Ala Gly
625                 630                 635                 640

Ala Gly Ser Gly Ala Gly Ala Gly Ser Gly Ala Gly Ala Gly Ser Gly
                645                 650                 655

Ala Gly Ala Gly Ser Gly Ala Gly Ala Gly Ser Gly Val Gly Val Pro
            660                 665                 670
```

-continued

Gly Val Gly Val Pro Gly Ala Gly Ala Gly Ser Gly Ala Gly
        675                 680                 685

Ser Gly Ala Gly Ala Gly Ser Gly Ala Gly Ala Gly Ser Gly Ala Gly
        690                 695                 700

Ala Gly Ser Gly Ala Gly Ala Gly Ser Gly Val Gly Val Pro Gly Val
705                 710                 715                 720

Gly Val Pro Gly Ala Gly Ala Gly Ser Gly Ala Gly Ala Gly Ser Gly
            725                 730                 735

Ala Gly Ala Gly Ser Gly Ala Gly Ala Gly Ser Gly Ala Gly Ala Gly
        740                 745                 750

Ser Gly Ala Gly Ala Gly Ser Gly Val Gly Val Pro Gly Val Gly Val
        755                 760                 765

Pro Gly Ala Gly Ala Gly Ser Gly Ala Gly Ala Gly Ser Gly Ala Gly
        770                 775                 780

Ala Gly Ser Gly Ala Gly Ala Gly Ser Gly Ala Gly Ala Gly Ser Gly
785                 790                 795                 800

Ala Gly Ala Gly Ser Gly Val Gly Val Pro Gly Val Gly Val Pro Gly
            805                 810                 815

Ala Gly Ala Gly Ser Gly Ala Gly Ala Gly Ser Gly Ala Gly Ala Gly
        820                 825                 830

Ser Gly Ala Gly Ala Gly Ser Gly Ala Gly Ala Gly Ser Gly Ala Gly
        835                 840                 845

Ala Gly Ser Gly Val Gly Val Pro Gly Val Gly Val Pro Gly Ala Gly
        850                 855                 860

Ala Gly Ser Gly Ala Gly Ala Gly Ser Gly Ala Gly Ala Gly Ser Gly
865                 870                 875                 880

Ala Gly Ala Gly Ser Gly Ala Gly Ala Gly Ser Gly Ala Gly Ala Gly
            885                 890                 895

Ser Gly Val Gly Val Pro Gly Val Gly Val Pro Gly Ala Gly Ala Gly
        900                 905                 910

Ser Gly Ala Gly Ala Gly Ser Gly Ala Gly Ala Gly Ser Gly Ala Gly
        915                 920                 925

Ala Gly Ser Gly Ala Gly Ala Gly Ser Gly Ala Gly Ala Gly Ser Gly
        930                 935                 940

Val Gly Val Pro Gly Val Gly Val Pro Gly Ala Gly Ala Gly Ser Gly
945                 950                 955                 960

Ala Gly Ala Gly Ser Gly Ala Gly Ala Gly Ser Gly Ala Gly Ala Gly
            965                 970                 975

Ser Gly Ala Gly Ala Gly Ser Gly Ala Gly Ala Gly Ser Gly Val Gly
        980                 985                 990

Val Pro Gly Val Gly Val Pro Gly Ala Gly Ala Gly Ser Gly Ala Gly
        995                 1000                1005

Ala Gly Ser Gly Ala Gly Ala Gly Ser Gly Ala Gly Ala Gly Ser
        1010                1015                1020

Gly Ala Gly Ala Gly Ser Gly Ala Gly Ala Gly Ser Gly Val Gly
        1025                1030                1035

Val Pro Gly Val Gly Val Pro Gly Ala Gly Ala Gly Ser Gly Ala
        1040                1045                1050

Gly Ala Gly Ser Gly Ala Gly Ala Gly Ser Gly Ala Gly Ala Gly
        1055                1060                1065

Ser Gly Ala Gly Ala Gly Ser Gly Ala Gly Ala Gly Ser Gly Val
        1070                1075                1080

-continued

Gly Val Pro Gly Val Gly Val Pro Gly Ala Gly Ala Gly Ser Gly
             1085                1090                1095

Ala Gly Ala Gly Ser Gly Ala Gly Ala Gly Ser Gly Ala Gly Ala
        1100                1105                1110

Gly Ser Gly Ala Gly Ala Gly Ser Gly Ala Gly Ala Gly Ser Gly
    1115                1120                1125

Val Gly Val Pro Gly Val Gly Val Pro Gly Ala Gly Ala Gly Ser
1130                1135                1140

Gly Ala Gly Ala Gly Ser Gly Ala Gly Ala Gly Ser Gly Ala Gly
        1145                1150                1155

Ala Gly Ser Gly Ala Gly Ala Gly Ser Gly Ala Gly Ala Gly Ser
    1160                1165                1170

Gly Val Gly Val Pro Gly Val Gly Val Pro Gly Ala Gly Ala Gly
1175                1180                1185

Ser Gly Ala Gly Ala Gly Ser Gly Ala Gly Ala Gly Ser Gly Ala
        1190                1195                1200

Gly Ala Gly Ser Gly Ala Gly Ala Gly Ser Gly Ala Gly Ala Gly
    1205                1210                1215

Ser Gly Val Gly Val Pro Gly Val Gly Val Pro Gly Ala Gly Ala
1220                1225                1230

Gly Ser Gly Ala Gly Ala Gly Ser Gly Ala Gly Ala Gly Ser Gly
        1235                1240                1245

Ala Gly Ala Gly Ser Gly Ala Gly Ala Gly Ser Gly Ala Gly Ala
    1250                1255                1260

Gly Ser Gly Val Gly Val Pro Gly Val Gly Val Pro Gly Ala Gly
1265                1270                1275

Ala Gly Ser Gly Ala Gly Ala Gly Ser Gly Ala Gly Ala Gly Ser
        1280                1285                1290

Gly Ala Gly Ala Gly Ser Gly Ala Gly Ala Gly Ser Gly Ala Gly
    1295                1300                1305

Ala Gly Ser Gly Val Gly Val Pro Gly Val Gly Val Pro Gly Ala
1310                1315                1320

Gly Ala Gly Ser Gly Ala Gly Ala Gly Ser Gly Ala Gly Ala Gly
        1325                1330                1335

Ser Gly Ala Gly Ala Gly Ser Gly Ala Gly Ala Gly Ser Gly Ala
    1340                1345                1350

Gly Ala Gly Ser Gly Val Gly Val Pro Gly Val Gly Val Pro Gly
1355                1360                1365

Ala Met Asp Pro Gly Arg Tyr Gln Asp Leu Arg Ser His His His
        1370                1375                1380

His His His
    1385

<210> SEQ ID NO 31
<211> LENGTH: 1292
<212> TYPE: PRT
<213> ORGANISM: Artificial sequence
<220> FEATURE:
<223> OTHER INFORMATION: Synthetic construct: protein(A)

<400> SEQUENCE: 31

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

```
Met Gly Ala Gly Ala Gly Ser Gly Ala Gly Ser Gly Ala Gly
         35                  40                  45
Ala Gly Ser Gly Ala Gly Ser Gly Ala Gly Ala Gly Ser Gly
 50                  55                  60
Ala Gly Ala Gly Ser Gly Ala Gly Ser Gly Ala Gly Ala Gly
 65                  70                  75                  80
Ser Gly Val Gly Val Pro Gly Val Gly Val Pro Gly Val Val
                 85                  90                  95
Gly Val Gly Val Pro Gly Val Gly Val Pro Gly Val Gly Pro Gly
                100                 105                 110
Val Gly Val Pro Gly Val Gly Val Pro Gly Val Gly Val Pro Gly Val
                115                 120                 125
Gly Val Pro Gly Val Gly Val Pro Gly Val Gly Val Pro Gly Val Gly
            130                 135                 140
Val Pro Gly Val Gly Val Pro Gly Val Gly Val Pro Gly Val Gly Val
145                 150                 155                 160
Pro Gly Val Gly Val Pro Gly Val Gly Val Pro Gly Val Gly Val Pro
                165                 170                 175
Gly Val Gly Val Pro Gly Val Gly Val Pro Gly Val Gly Val Pro Gly
            180                 185                 190
Val Gly Val Pro Gly Val Gly Val Pro Gly Val Gly Val Pro Gly Val
            195                 200                 205
Gly Val Pro Gly Val Gly Val Pro Gly Val Gly Val Pro Gly Val Gly
            210                 215                 220
Val Pro Gly Val Gly Val Pro Gly Val Gly Val Pro Gly Val Gly Val
225                 230                 235                 240
Pro Gly Val Gly Val Pro Gly Val Gly Val Pro Gly Val Gly Val Pro
                245                 250                 255
Gly Val Gly Val Pro Gly Val Gly Val Pro Gly Val Gly Val Pro Gly
            260                 265                 270
Val Gly Val Pro Gly Val Gly Val Pro Gly Ala Gly Ala Gly Ser Gly
            275                 280                 285
Ala Gly Ala Gly Ser Gly Ala Gly Ala Gly Ser Gly Ala Gly Ala Gly
 290                 295                 300
Ser Gly Ala Gly Ala Gly Ser Gly Ala Gly Ala Gly Ser Gly Ala Gly
305                 310                 315                 320
Ala Gly Ser Gly Ala Gly Ala Gly Ser Gly Val Gly Val Pro Gly Val
                325                 330                 335
Gly Val Pro Gly Val Gly Val Pro Gly Val Gly Val Pro Gly Val Gly
            340                 345                 350
Val Pro Gly Val Gly Val Pro Gly Val Gly Val Pro Gly Val Gly Val
            355                 360                 365
Pro Gly Val Gly Val Pro Gly Val Gly Val Pro Gly Val Gly Val Pro
        370                 375                 380
Gly Val Gly Val Pro Gly Val Gly Val Pro Gly Val Gly Val Pro Gly
385                 390                 395                 400
Val Gly Val Pro Gly Val Gly Val Pro Gly Val Gly Val Pro Gly Val
                405                 410                 415
Gly Val Pro Gly Val Gly Val Pro Gly Val Gly Val Pro Gly Val Gly
            420                 425                 430
Val Pro Gly Val Gly Val Pro Gly Val Gly Val Pro Gly Val Gly Val
            435                 440                 445
Pro Gly Val Gly Val Pro Gly Val Gly Val Pro Gly Val Gly Val Pro
```

```
            450                 455                 460
Gly Val Gly Val Pro Gly Val Gly Val Pro Gly Val Gly Val Pro Gly
465                 470                 475                 480

Val Gly Val Pro Gly Val Gly Val Pro Gly Val Gly Val Pro Gly Val
                485                 490                 495

Gly Val Pro Gly Val Gly Val Pro Gly Val Gly Val Pro Gly Val Gly
            500                 505                 510

Val Pro Gly Val Gly Val Pro Gly Val Gly Val Pro Gly Val Gly Val
        515                 520                 525

Pro Gly Ala Gly Ala Gly Ser Gly Ala Gly Ala Gly Ser Gly Ala Gly
    530                 535                 540

Ala Gly Ser Gly Ala Gly Ala Gly Ser Gly Ala Gly Ala Gly Ser Gly
545                 550                 555                 560

Ala Gly Ala Gly Ser Gly Ala Gly Ala Gly Ser Gly Ala Gly Ala Gly
                565                 570                 575

Ser Gly Val Gly Val Pro Gly Val Gly Val Pro Gly Val Gly Val Pro
            580                 585                 590

Gly Val Gly Val Pro Gly Val Gly Val Pro Gly Val Gly Val Pro Gly
        595                 600                 605

Val Gly Val Pro Gly Val Gly Val Pro Gly Val Gly Val Pro Gly Val
    610                 615                 620

Gly Val Pro Gly Val Gly Val Pro Gly Val Gly Val Pro Gly Val Gly
625                 630                 635                 640

Val Pro Gly Val Gly Val Pro Gly Val Gly Val Pro Gly Val Gly Val
                645                 650                 655

Pro Gly Val Gly Val Pro Gly Val Gly Val Pro Gly Val Gly Val Pro
            660                 665                 670

Gly Val Gly Val Pro Gly Val Gly Val Pro Gly Val Gly Val Pro Gly
        675                 680                 685

Val Gly Val Pro Gly Val Gly Val Pro Gly Val Gly Val Pro Gly Val
    690                 695                 700

Gly Val Pro Gly Val Gly Val Pro Gly Val Gly Val Pro Gly Val Gly
705                 710                 715                 720

Val Pro Gly Val Gly Val Pro Gly Val Gly Val Pro Gly Val Gly Val
                725                 730                 735

Pro Gly Val Gly Val Pro Gly Val Gly Val Pro Gly Val Gly Val Pro
            740                 745                 750

Gly Val Gly Val Pro Gly Val Gly Val Pro Gly Val Gly Val Pro Gly
        755                 760                 765

Val Gly Val Pro Gly Val Gly Val Pro Gly Ala Gly Ala Gly Ser Gly
    770                 775                 780

Ala Gly Ala Gly Ser Gly Ala Gly Ala Gly Ser Gly Ala Gly Ala Gly
785                 790                 795                 800

Ser Gly Ala Gly Ala Gly Ser Gly Ala Gly Ala Gly Ser Gly Ala Gly
                805                 810                 815

Ala Gly Ser Gly Ala Gly Ala Gly Ser Gly Val Gly Val Pro Gly Val
            820                 825                 830

Gly Val Pro Gly Val Gly Val Pro Gly Val Gly Val Pro Gly Val Gly
        835                 840                 845

Val Pro Gly Val Gly Val Pro Gly Val Gly Val Pro Gly Val Gly Val
    850                 855                 860

Pro Gly Val Gly Val Pro Gly Val Gly Val Pro Gly Val Gly Val Pro
865                 870                 875                 880
```

-continued

Gly Val Gly Val Pro Gly Val Gly Val Pro Gly Val Gly Val Pro Gly
                885                 890                 895

Val Gly Val Pro Gly Val Gly Val Pro Gly Val Gly Val Pro Gly Val
            900                 905                 910

Gly Val Pro Gly Val Gly Val Pro Gly Val Gly Val Pro Gly Val Gly
        915                 920                 925

Val Pro Gly Val Gly Val Pro Gly Val Gly Val Pro Gly Val Gly Val
    930                 935                 940

Pro Gly Val Gly Val Pro Gly Val Gly Val Pro Gly Val Gly Val Pro
945                 950                 955                 960

Gly Val Gly Val Pro Gly Val Gly Val Pro Gly Val Gly Val Pro Gly
                965                 970                 975

Val Gly Val Pro Gly Val Gly Val Pro Gly Val Gly Val Pro Gly Val
            980                 985                 990

Gly Val Pro Gly Val Gly Val Pro  Gly Val Gly Val Pro  Gly Val Gly
        995                 1000                1005

Val Pro  Gly Val Gly Val Pro  Gly Val Gly Val Pro  Gly Val Gly
    1010                1015                1020

Val Pro  Gly Ala Gly Ala Gly  Ser Gly Ala Gly Ala  Gly Ser Gly
    1025                1030                1035

Ala Gly  Ala Gly Ser Gly Ala  Gly Ala Gly Ser Gly  Ala Gly Ala
    1040                1045                1050

Gly Ser  Gly Ala Gly Ala Gly  Ser Gly Ala Gly Ala  Gly Ser Gly
    1055                1060                1065

Ala Gly  Ala Gly Ser Gly Val  Gly Val Pro Gly Val  Gly Val Pro
    1070                1075                1080

Gly Val  Gly Val Pro Gly Val  Gly Val Pro Gly Val  Gly Val Pro
    1085                1090                1095

Gly Val  Gly Val Pro Gly Val  Gly Val Pro Gly Val  Gly Val Pro
    1100                1105                1110

Gly Val  Gly Val Pro Gly Val  Gly Val Pro Gly Val  Gly Val Pro
    1115                1120                1125

Gly Val  Gly Val Pro Gly Val  Gly Val Pro Gly Val  Gly Val Pro
    1130                1135                1140

Gly Val  Gly Val Pro Gly Val  Gly Val Pro Gly Val  Gly Val Pro
    1145                1150                1155

Gly Val  Gly Val Pro Gly Val  Gly Val Pro Gly Val  Gly Val Pro
    1160                1165                1170

Gly Val  Gly Val Pro Gly Val  Gly Val Pro Gly Val  Gly Val Pro
    1175                1180                1185

Gly Val  Gly Val Pro Gly Val  Gly Val Pro Gly Val  Gly Val Pro
    1190                1195                1200

Gly Val  Gly Val Pro Gly Val  Gly Val Pro Gly Val  Gly Val Pro
    1205                1210                1215

Gly Val  Gly Val Pro Gly Val  Gly Val Pro Gly Val  Gly Val Pro
    1220                1225                1230

Gly Val  Gly Val Pro Gly Val  Gly Val Pro Gly Val  Gly Val Pro
    1235                1240                1245

Gly Val  Gly Val Pro Gly Val  Gly Val Pro Gly Val  Gly Val Pro
    1250                1255                1260

Gly Val  Gly Val Pro Gly Val  Gly Val Pro Gly Ala  Met Asp Pro
    1265                1270                1275

```
Gly Arg  Tyr Gln Asp Leu Arg  Ser His His His  His His
    1280             1285             1290
```